(12) United States Patent
Hosseinzadeh Taher et al.

(10) Patent No.: US 11,436,725 B2
(45) Date of Patent: Sep. 6, 2022

(54) SYSTEMS, METHODS, AND APPARATUSES FOR IMPLEMENTING A SELF-SUPERVISED CHEST X-RAY IMAGE ANALYSIS MACHINE-LEARNING MODEL UTILIZING TRANSFERABLE VISUAL WORDS

(71) Applicant: Arizona Board of Regents on Behalf of Arizona State University, Scottsdale, AZ (US)

(72) Inventors: Mohammad Reza Hosseinzadeh Taher, Tempe, AZ (US); Fatemeh Haghighi, Tempe, AZ (US); Jianming Liang, Scottsdale, AZ (US)

(73) Assignee: Arizona Board of Regents on behalf of Arizona State University, Scottsdale, AZ (US)

( * ) Notice: Subject to any disclaimer, the term of this patent is extended or adjusted under 35 U.S.C. 154(b) by 11 days.

(21) Appl. No.: 17/098,422

(22) Filed: Nov. 15, 2020

(65) Prior Publication Data
US 2021/0150710 A1 May 20, 2021

Related U.S. Application Data

(60) Provisional application No. 62/980,099, filed on Feb. 21, 2020, provisional application No. 62/936,301, filed on Nov. 15, 2019.

(51) Int. Cl.
*G06T 7/00* (2017.01)
*G06T 7/73* (2017.01)
*A61B 6/00* (2006.01)

(52) U.S. Cl.
CPC ............ *G06T 7/0012* (2013.01); *A61B 6/468* (2013.01); *A61B 6/50* (2013.01); *G06T 7/74* (2017.01);
(Continued)

(58) Field of Classification Search
CPC ............. G06T 7/0012; G06T 7/74; G06T 2207/10116; G06T 2207/20081;
(Continued)

(56) References Cited

U.S. PATENT DOCUMENTS

| 2019/0057504 A1* | 2/2019 | Kobayashi | ........... G06K 9/6271 |
| 2020/0184262 A1* | 6/2020 | Chui | .................... A61B 5/0062 |

* cited by examiner

*Primary Examiner* — Siamak Harandi
(74) *Attorney, Agent, or Firm* — Elliott, Ostrander & Preston, P.C.

(57) ABSTRACT

Not only is annotating medical images tedious and time consuming, but it also demands costly, specialty-oriented expertise, which is not easily accessible. To address this challenge, a new self-supervised framework is introduced: TransVW (transferable visual words), exploiting the prowess of transfer learning with convolutional neural networks and the unsupervised nature of visual word extraction with bags of visual words, resulting in an annotation-efficient solution to medical image analysis. TransVW was evaluated using NIH ChestX-ray14 to demonstrate its annotation efficiency. When compared with training from scratch and ImageNet-based transfer learning, TransVW reduces the annotation efforts by 75% and 12%, respectively, in addition to significantly accelerating the convergence speed. More importantly, TransVW sets new records: achieving the best average AUC on all 14 diseases, the best individual AUC scores on 10 diseases, and the second best individual AUC scores on 3 diseases. This performance is unprecedented, because heretofore no self-supervised learning method has outperformed ImageNet-based transfer learning and no annotation reduction has been reported for self-supervised learning. These achievements are contributable to a simple yet powerful observation: The complex and recurring anatomical structures in medical images are natural visual words, which can be automatically extracted, serving as strong yet free supervision signals for CNNs to learn gen- (Continued)

eralizable and transferable image representation via self-supervision.

20 Claims, 27 Drawing Sheets

(52) U.S. Cl.
CPC ............... *G06T 2207/10116* (2013.01); *G06T 2207/20081* (2013.01); *G06T 2207/20084* (2013.01); *G06T 2207/30061* (2013.01)

(58) Field of Classification Search
CPC . G06T 2207/20084; G06T 2207/30061; A61B 6/468; A61B 6/50; G06V 2201/033; G06V 10/464; G06V 10/82; G06K 9/6271

See application file for complete search history.

FIG. 1B
FIG. 1C
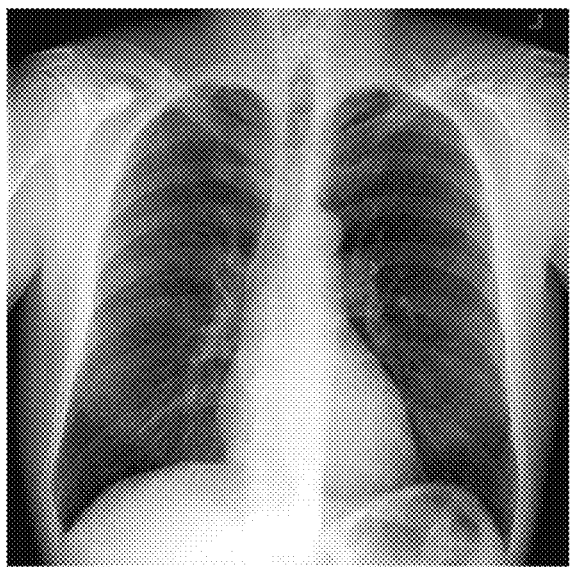
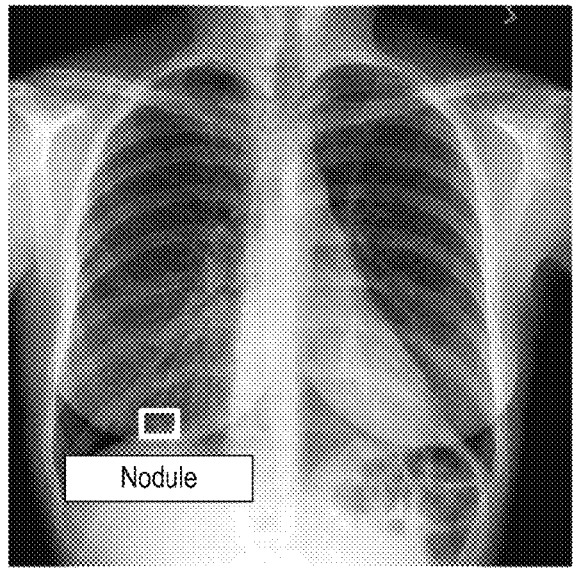
FIG. 1D
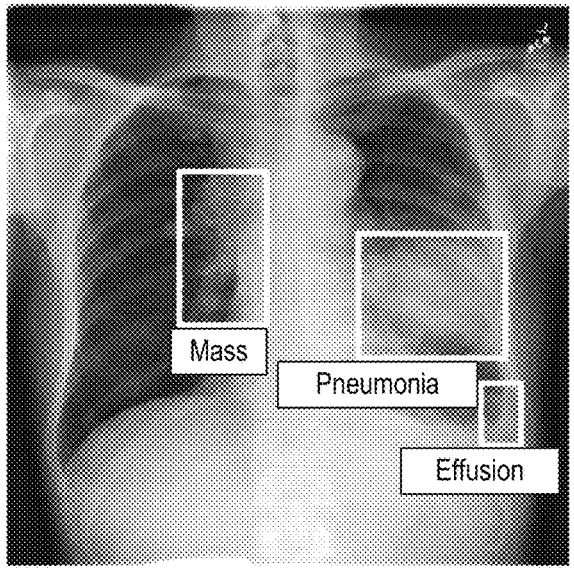
FIG. 1E

800

Algorithm 1 Coordinate-based visual words extraction

1: Inputs:
   $X_{tr}^1$: part 1 of train set
   $N$: number of instances of each visual word
   $M$: number of visual word classes
2: Outputs:
   $W_c, I_c$: Extracted visual words and their IDs
3: Initialize:
   $W_c, I_c = [\ ]$
   coordinates $= \emptyset$
   $cntr = 0$
4: for $i = 0$ to $M - 1$ do
5:     $t = \emptyset$
6:     $im \leftarrow$ select a random image from $X_{tr}^1$
7:     $t \leftarrow N$ most similar images to $im$ from $X_{tr}^1$
8:     while True do
9:        $(x_i, y_i) = random()$
10:        if $(x_i, y_i)$ not in *coordinates* then
11:           *coordinates*.insert($(x_i, y_i)$)
12:           break
13:        end if
14:     end while
15:     for each image in $t$ do
16:        $W_c[cntr] \leftarrow$ Extract patch around $(x_i, y_i)$ coordinate
17:        $I_c[cntr] \leftarrow i$
18:        $cntr + +$
19:     end for
20: end for

FIG. 8A

Algorithm 2 Anatomy-aware visual words extraction

1: Inputs:
   $X_{tr}^2$: part 2 of train set
   $K$: number of instances of each visual word
   $M$: number of visual word classes
   $\mathcal{M}$: CVW classifier
2: Outputs:
   $W_a, I_a$: Extracted visual words and their IDs
3: Initialize:
   $W_a, I_a = [\,]$
   $probs = [\,], vws = [\,]$
   $L = 10,000$
4: for each i = 0 to L: do
5:    $patches = [\,]$
6:    $im \leftarrow$ select a random image from $X_{tr}^2$
7:    $patches \leftarrow$ Slide a window on $im$ to get $p$ patches
8:    $pred_i \leftarrow \mathcal{M}(patches)$
9:    for $c = 0$ to $M - 1$ do
10:      $probs[i][c] \leftarrow max(pred_i[:][c])$
11:      $vws[i][c] \leftarrow patches[arg\_max(pred_i[:][c])]$
12:    end for
13: end for
14: for $c = 0$ to $M - 1$ do
15:    $patch_c \leftarrow$ find $K$ most confident patches of class $c$ from
16:    $vws$ based on their probabilities in $probs$
17:    $W_a$.insert($patch_c$)
18:    $I_a$.insert(c)
19: end for

FIG. 8B

Table 1

| Method | Arch | Init | Atel | Card | Effu | Infi | Mass | Nodu | Pneu1 | Pneu2 | Cons | Edem | Emph | Fibr | PT | Hern | Mean |
|---|---|---|---|---|---|---|---|---|---|---|---|---|---|---|---|---|---|
| 1: | RN-50 | ImageNet | 0.700 | 0.810 | 0.759 | 0.661 | 0.693 | 0.669 | 0.658 | 0.799 | 0.703 | 0.805 | 0.833 | 0.786 | 0.684 | 0.872 | 0.745 |
| 2: | RN-50 | ImageNet | 0.727 | 0.836 | 0.789 | 0.672 | 0.776 | 0.696 | 0.649 | 0.808 | 0.720 | 0.806 | 0.888 | 0.771 | 0.737 | 0.693 | 0.755 |
| 3: | RN-152 | ImageNet | 0.751 | 0.871 | 0.818 | 0.682 | 0.799 | 0.715 | 0.694 | 0.825 | 0.742 | 0.835 | 0.843 | 0.804 | 0.746 | 0.902 | 0.788 |
| 4: | RN-101 | ImageNet | 0.763 | 0.884 | 0.816 | 0.679 | 0.801 | 0.729 | 0.710 | 0.838 | 0.744 | 0.841 | 0.884 | 0.801 | 0.754 | 0.876 | 0.794 |
| 5: | RN-50 | ImageNet | 0.756 | 0.887 | 0.819 | 0.689 | 0.814 | 0.755 | 0.729 | 0.850 | 0.728 | 0.848 | 0.908 | 0.818 | 0.765 | 0.875 | 0.803 |
| 6: | RN-38 | Scratch | 0.763 | 0.875 | 0.822 | 0.694 | 0.820 | 0.747 | 0.714 | 0.840 | 0.749 | 0.846 | 0.895 | 0.816 | 0.763 | 0.937 | 0.806 |
| 7: | DN-121 | ImageNet | 0.767 | 0.883 | 0.828 | 0.709 | 0.821 | 0.758 | 0.731 | 0.846 | 0.745 | 0.835 | 0.895 | 0.818 | 0.761 | 0.896 | 0.807 |
| 8: | DN-121 | ImageNet | 0.781 | 0.883 | 0.831 | 0.697 | 0.830 | 0.764 | 0.725 | 0.866 | 0.758 | 0.853 | 0.911 | 0.826 | 0.780 | 0.918 | 0.816 |
| As Described: | DN-121 | TransVW | 0.787 | 0.881 | 0.841 | 0.699 | 0.831 | 0.792 | 0.731 | 0.878 | 0.754 | 0.856 | 0.935 | 0.844 | 0.802 | 0.922 | 0.825 |

† Abbreviation of each pathology is as follow: Atel: Atelectasis; Card: Cardiomegaly; Effu: Effusion; Infi: Infiltration; Nodu: Nodule; Pneu1: Pneumonia; Pneu2: Pneumothorax; Cons: Consolidation; Edem: Edema; Emph: Emphysema; Fibr: Fibrosis; PT: Pleural Thickening; Hern: Hernia

FIG. 9A

Table 2

| Training Data | Model | Task | Initialization | Goal |
|---|---|---|---|---|
| Part 1 (w/o disease labels) | CVW Classifier (Figure 3) | Pretext | Scratch | Enhance consistency of visual word instances (Figs. 10A-10D) |
| Part 2 (w/o disease labels) | AVW Classifier (Figure 4) | Pretext | Scratch | Learn Consistent visual words (Figure 6) |
| Part 2 (w/o disease labels) | ADS (Figure 5) | Pretext | AVW Classifier | Improve representation learning (Table 2) |
| All (with disease labels) | Target model | Target | TransVW (ADS encoder) | Classify thorax diseases (table 1) |

FIG. 9B

Table 3

| Training Data | Mean AUC(%) | | |
|---|---|---|---|
| | Scratch | ImageNet | TransVW |
| 25% | 69.05 ± 6.3 | 78.17 ± 0.52 | 78.52 ± 0.35 |
| p-value[†] | 5.51e-04 | 0.0465 | N/A |
| 50% | 75.43 ± 1.6 | 80.10 ± 0.41 | 80.37 ± 0.24 |
| p-value[†] | 3.12e-05 | 0.0442 | N/A |
| 75% | 77.73 ± 0.74 | 80.87 ± 0.29 | 81.12 ± 0.25 |
| p-value[†] | 4.06e-09 | 0.0354 | N/A |
| 88% | 78.14 ± 0.70 | 81.29 ± 0.14 | 81.51 ± 0.14 |
| p-value[†] | 8.00e-07 | 0.0020 | N/A |
| 100% | 78.59 ± 0.66 | 81.64 ± 0.21 | 81.86 ± 0.15 |
| p-value[†] | 1.78e-08 | 0.0067 | N/A |

[†] These p-values are calculated between our TransVW vs. scratch and ImageNet.

FIG. 9C

Table 4A

| Initialization | Mean AUC(%) | p-value[†] | p-value[‡] |
|---|---|---|---|
| Scratch | 77.58 ± 0.45 | N/A | 0.0261 |
| Rotation[*] | 77.61 ± 0.19 | 0.4411 | 0.0103 |
| Inpainting[*] | 77.39 ± 0.23 | 0.1712 | 0.0065 |
| Jigsaw[*] | 76.47 ± 2.04 | 0.0835 | 0.0298 |
| AVW (our) | 78.10 ± 0.51 | 0.0261 | N/A |

* The methodology described herein was applied to the chest X-ray images.

[†] These p-values are calculated between random initialization vs. self-supervised methods; AVW is the only method which is significantly better than scratch.

[‡] These p-values are calculated between fine-tuning from AVW vs. training from scratch and other self-supervised methods.

FIG. 9D

Table 4B

| Initialization | Mean AUC(%) | $p$-value[†] | $p$-value[‡] |
|---|---|---|---|
| Scratch | 77.58 ± 0.45 | N/A | 8.83e-8 |
| Rotation | 77.61 ± 0.19 | 0.4411 | 0 |
| Inpainting | 77.39 ± 0.23 | 0.1712 | 2.81e-8 |
| Jigsaw | 76.47 ± 2.04 | 0.0835 | 0.0043 |
| AVW | 78.10 ± 0.51 | 0.0261 | 9.36e-5 |
| TransVW | 79.14 ± 0.23 | 8.83e-8 | N/A |

[†] $p$-values are calculated between scratch vs. self-supervised methods.
[‡] $p$-values are calculated between fine-tuning from TransVW vs. other methods.

FIG. 9E

Table 5

| Initialization | Mean AUC(%) | p-value[†] |
|---|---|---|
| AE | 76.71 ± 0.34 | 0.0001 |
| AE+AVW | 77.76 ± 0.59 | |
| Inpainting | 77.39 ± 0.23 | 0.0260 |
| Inpainting+AVW | 78.02 ± 0.50 | |
| Elastic | 78.01 ± 0.26 | 3.31e-08 |
| Elastic+AVW | 79.14 ± 0.23 | |

[†] These *p*-values are calculated between the image restoration task with and without combining with AVW.

Table 6A

| Initialization | Mean AUC(%) | p-value |
|---|---|---|
| Scratch | 78.59±0.66 | 1.78e-08 |
| ImageNet | 81.64±0.21 | 0.0067 |
| TransVW | 81.86±0.15 | - |

(a) Performance: Fine-tuning models from TransVW significantly outperforms fine-tuning models from ImageNet and training from scratch.

Table 6B

| Initialization | Training Epochs | p-value |
|---|---|---|
| Scratch | 18.9±3.48 | 9.58e-6 |
| ImageNet | 8.0±2.05 | 0.0342 |
| TransVW | 6.5±1.27 | - |

(b) Training time: TransVW significantly accelerates the training time of target task in comparison with ImageNet-based transfer learning and training from scratch.

Table 6C

| Initialization | Training data(%) | Mean AUC(%) | p-value |
|---|---|---|---|
| Scratch | 100 | 78.59±0.66 | 0.3802 |
| TransVW | 25 | 78.52±0.35 | |
| ImageNet | 100 | 81.64±0.21 | 0.1171 |
| TransVW | 88 | 81.51±0.14 | |

(c) Annotation saving: With 25% and 88% of labeled training data, TransVW achieves the target performance equivalent to training from scratch and fine-tuning pre-trained ImageNet models using 100% of training data, respectively.

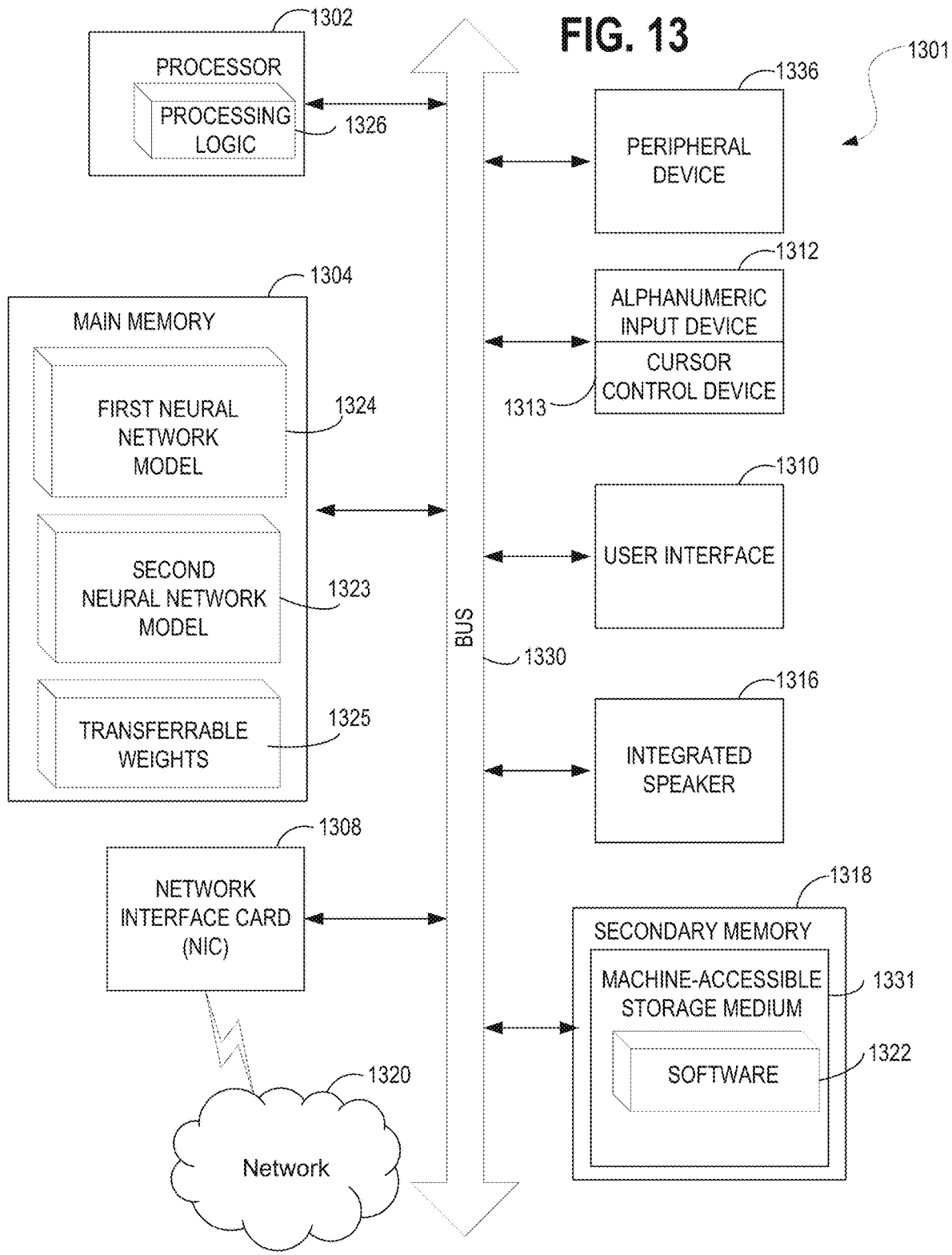

SYSTEMS, METHODS, AND APPARATUSES FOR IMPLEMENTING A SELF-SUPERVISED CHEST X-RAY IMAGE ANALYSIS MACHINE-LEARNING MODEL UTILIZING TRANSFERABLE VISUAL WORDS

CLAIM OF PRIORITY

This U.S. Utility Patent Application is related to, and claims priority to, the U.S. Provisional Patent Application Ser. No. 62/936,301, entitled "SYSTEMS, METHODS, AND APPARATUSES FOR IMPLEMENTING A SELF-SUPERVISED CHEST X-RAY IMAGE ANALYSIS MACHINE-LEARNING MODEL UTILIZING LEARNED TRANSFERABLE VISUAL WORDS," filed Nov. 15, 2019 and is further related to, and claims priority to, the U.S. Provisional Patent Application Ser. No. 62/980,099, entitled "SYSTEMS, METHODS, AND APPARATUSES FOR IMPLEMENTING AN ANNOTATION-EFFICIENT SOLUTION FOR CHEST X-RAY IMAGE ANALYSIS UTILIZING LEARNED TRANSFERABLE VISUAL WORDS," filed Feb. 21, 2020, the entire contents of each being incorporated herein by reference.

GOVERNMENT RIGHTS AND GOVERNMENT AGENCY SUPPORT NOTICE

This invention was made with government support under R01 HL128785 awarded by the National Institutes of Health. The government has certain rights in the invention.

COPYRIGHT NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

TECHNICAL FIELD

Embodiments of the invention relate generally to the field of medical imaging and analysis using convolutional neural networks for the classification and annotation of medical images, and more particularly, to systems, methods, and apparatuses for implementing a self-supervised chest x-ray image analysis machine-learning model utilizing transferable learned CNN model weight representing visual words.

BACKGROUND

The subject matter discussed in the background section should not be assumed to be prior art merely as a result of its mention in the background section. Similarly, a problem mentioned in the background section or associated with the subject matter of the background section should not be assumed to have been previously recognized in the prior art. The subject matter in the background section merely represents different approaches, which in and of themselves may also correspond to embodiments of the claimed inventions.

Machine learning models have various applications to automatically process inputs and produce outputs considering situational factors and learned information to improve output quality. One area where machine learning models, and neural networks in particular, provide high utility is in the field of processing medical images.

Within the context of machine learning and with regard to deep learning specifically, a Convolutional Neural Network (CNN, or ConvNet) is a class of deep neural networks, very often applied to analyzing visual imagery. Convolutional Neural Networks are regularized versions of multilayer perceptrons. Multilayer perceptrons are fully connected networks, such that each neuron in one layer is connected to all neurons in the next layer, a characteristic which often leads to a problem of overfitting of the data and the need for model regularization. Convolutional Neural Networks also seek to apply model regularization, but with a distinct approach. Specifically, CNNs take advantage of the hierarchical pattern in data and assemble more complex patterns using smaller and simpler patterns. Consequently, on the scale of connectedness and complexity, CNNs are on the lower extreme.

Conversely, the Bag of Visual Words (BoVW) model in the context of machine learning operates by representing an image as a set of features. Such features consist of keypoints and descriptors, in which keypoints are the "stand out" points in an image. Therefore, no matter how the image is rotated, shrunk, or expanded, its keypoints will always be the same. Descriptors represent the description of each respective keypoint. Keypoints and descriptors are then utilized to construct vocabularies via which to represent each image as a frequency histogram of features for that specific image. Using the frequency histogram, it is then possible to find and identify other similar images or predict the category of a never before seen image.

While existing Bag-of-Visual-Word (BoVW) models are capable of extracting such feature descriptors from input images and clustering those features construct a visual dictionary, the existing models have notable shortcomings. For instance, a significant drawback of existing BoVW models is that the extracted visual words cannot be fine-tuned, as is permissible with a learned deep model. In addition, the extracted visual words may not be intuitive nor explainable from the medical perspective, as they are automatically determined via unsupervised clustering algorithms.

Heretofore, self-supervised learning has been sparsely applied in the field of medical imaging. Nevertheless, there is a massive need to provide automated analysis to medical imaging with a high degree of accuracy so as to improve diagnosis capabilities, control medical costs, and to reduce workload burdens placed upon medical professionals.

Not only is annotating medical images tedious and time consuming, but it also demands costly, specialty-oriented expertise, which is not easily accessible. To address this challenge, a new self-supervised framework is introduced, referred to herein as TransVW or "transferable visual words," which operates by exploiting the prowess of transfer learning with convolutional neural networks and the unsupervised nature of visual word extraction with bags of visual words, resulting in an annotation-efficient solution, especially in the context of medical image analysis.

Problematically, improving chest X-ray classification without using pre-trained ImageNet models and reconciling the opposing features of CNNs and BoVW to amplify their strengths has not been explored in the conventional arts and no solutions are presently available to the marketplace. Further still, annotating medical imaging is tedious and time consuming, and demands costly, specialty-oriented knowledge and skills, which are not easily accessible. Furthermore, any misdiagnosis from failure to recognize or correctly identify anatomical structures and abnormalities may result in potentially devastating impacts on patient morbidity and mortality.

Embodiments described herein therefore provide enhanced solutions to improve upon conventionally known image representation and learning techniques by advantageously integrating modified CNNs and BoVW models to amplify their respective strengths, leading to more powerful solutions to applications, especially in the field of medical imaging. For instance, described herein are new methodologies utilizing transferable visual words learned by the CNN model (e.g., also referred to as "TransVW" herein). Use of the transferable visual words as described herein is based on the simple yet powerful observation that segments of sophisticated, consistent and recurrent anatomical structures in medical images are natural visual words or common anatomical patterns which can be automatically extracted, serving as strong yet free supervision signals enabling CNNs to learn generalizable image representations via self-supervision machine learning techniques. These learned image representations may then be transferred to application-specific target tasks by distilling transferable features via self-supervised learning.

The present state of the art may therefore benefit from implementing an annotation-efficient solution for chest x-ray image analysis utilizing learned transferable visual words as is described herein.

BRIEF DESCRIPTION OF THE DRAWINGS

Embodiments are illustrated by way of example, and not by way of limitation, and can be more fully understood with reference to the following detailed description when considered in connection with the figures in which:

FIGS. 1B, 1C, 1D, and 1E depict alternative exemplary visualizations of the lungs in an annotated chest X-ray in accordance with described embodiments;

FIG. 8A depicts an algorithm for CVW extraction in accordance with described embodiments;

FIG. 8B depicts an algorithm for AVW extraction in accordance with described embodiments;

FIG. 9A sets forth Table 1, which lists the mean performances of TransVW compared to SOTA across 14 pulmonary pathologies from the ChestX-ray14 Dataset, according to described embodiments;

FIG. 9B sets forth Table 2, which lists the division of Chest-Xray14 training data for training of classifiers and ADS encoder for performance of tasks to achieve the goals of TransVW, according to described embodiments;

FIG. 9C sets forth Table 3, which details how TransVW outperforms the models trained from scratch or pre-trained with ImageNet, according to described embodiments;

FIG. 9D sets forth Table 4A, which details how AVW outperforms the models trained from scratch or fine-tuned from other self-supervised methods, according to described embodiments;

FIG. 9E sets forth Table 4B, which demonstrates that fine-tuning from TransVW significantly outperforms fine-tuning from other self-supervised approaches on the ChestX-ray14 multi-label pathology classification task, according to described embodiments;

FIG. 9F sets forth Table 5 which details the contribution of AVW in the performance of ADS, in accordance with described embodiments;

FIG. 9G sets forth Tables 6A, 6B, and 6C, which detail the performance (a), training time (b), and the annotation savings (c) provided through the use of the TransVW methodology over ImageNet or by training from scratch, in accordance with described embodiments;

FIG. 13 illustrates a diagrammatic representation of a machine 1301 in the exemplary form of a computer system, in accordance with one embodiment.

DETAILED DESCRIPTION

Described herein are methods and systems for implementing an annotation-efficient solution for chest x-ray image analysis utilizing learned transferable visual words.

Generally speaking, through the transfer learning processes described below, the weights of a pre-trained Convolutional Neural Network (CNN) model are transferred to a second CNN network. The second CNN network is then fine-tuned with labeled data to perform the target task, which as will be described below, is a supervised classification (e.g., a chest X-ray thorax classification). Consequently, after transferring the TransVW weights to the target CNN network, the target network will be fine-tuned with labeled data and then will be tested on the previously unseen images which test results show achieves a higher performance than previously known methods.

To address the annotation challenge associated with medical imaging, an annotation-efficient solution to chest image analysis is utilized. Such a technique is based on a simple yet powerful observation, which is illustrated at FIGS. 1A through 1E below. Notably, it is observed that the sophisticated and recurrent anatomical structures in medical images are natural visual words, which may be automatically extracted, serving as strong yet free supervision signals for convolutional neural networks (CNNs) by which to learn generalizable image representation via self-supervision. The learned image representation may then be transferred to application-specific target tasks.

According to an exemplary embodiment, there is a system having at least a processor and a memory therein to execute instructions, wherein such a system is specially configured with means for executing, via the processor, a Convolutional Neural Network (CNN) model stored within the memory of the system, wherein the CNN model is self-supervised for generalizable and transferable image representation of medical images; means for identifying visual words via the executing CNN model, wherein the visual words are consistent and recurring patterns involving anatomical structures across medical images; means for transferring learned weights from the CNN model representing identified visual words from an initial CNN model to another CNN model capable of performing the "target task" for diagnosis of disease by fine-tuning the transferred weights, wherein instances of the visual words correspond to sample patches of images extracted across multiple different images for the same visual word.

Figure 3:
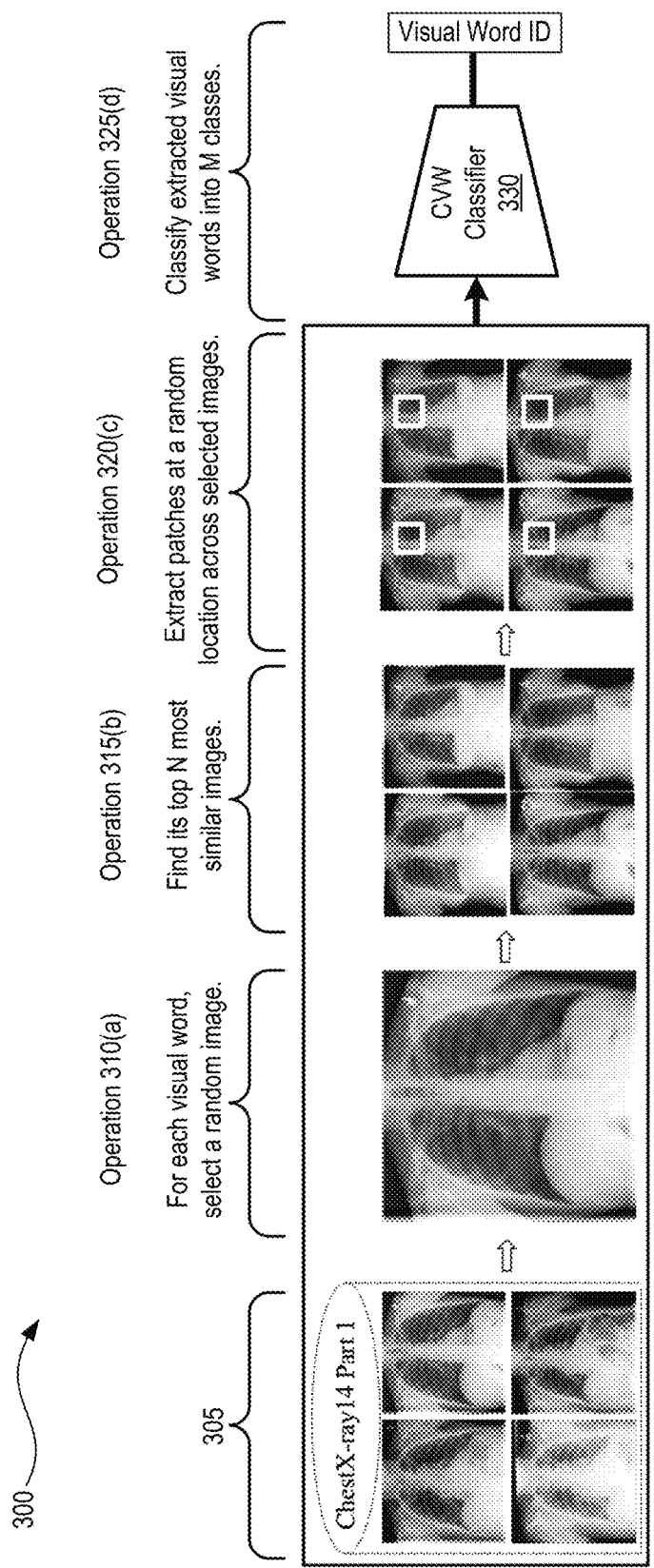
FIG. 3 depicts use and application of a Coordinate-based Visual Word (CVW) classifier in accordance with described embodiments.
Figure 4:
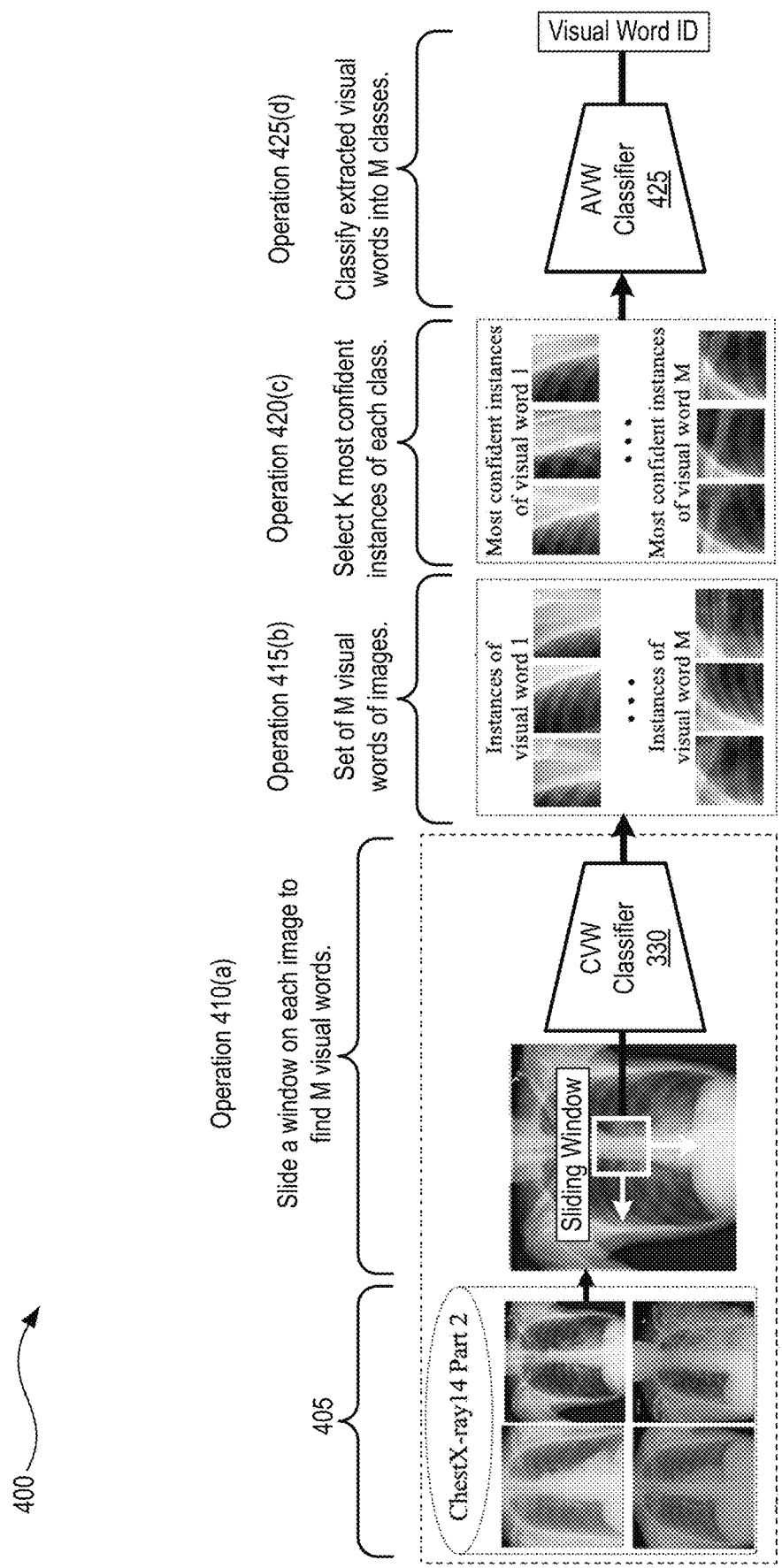
FIG. 4 depicts use and application of an anatomy-aware visual word (AVW) classifier in accordance with described embodiments.
Figure 5:
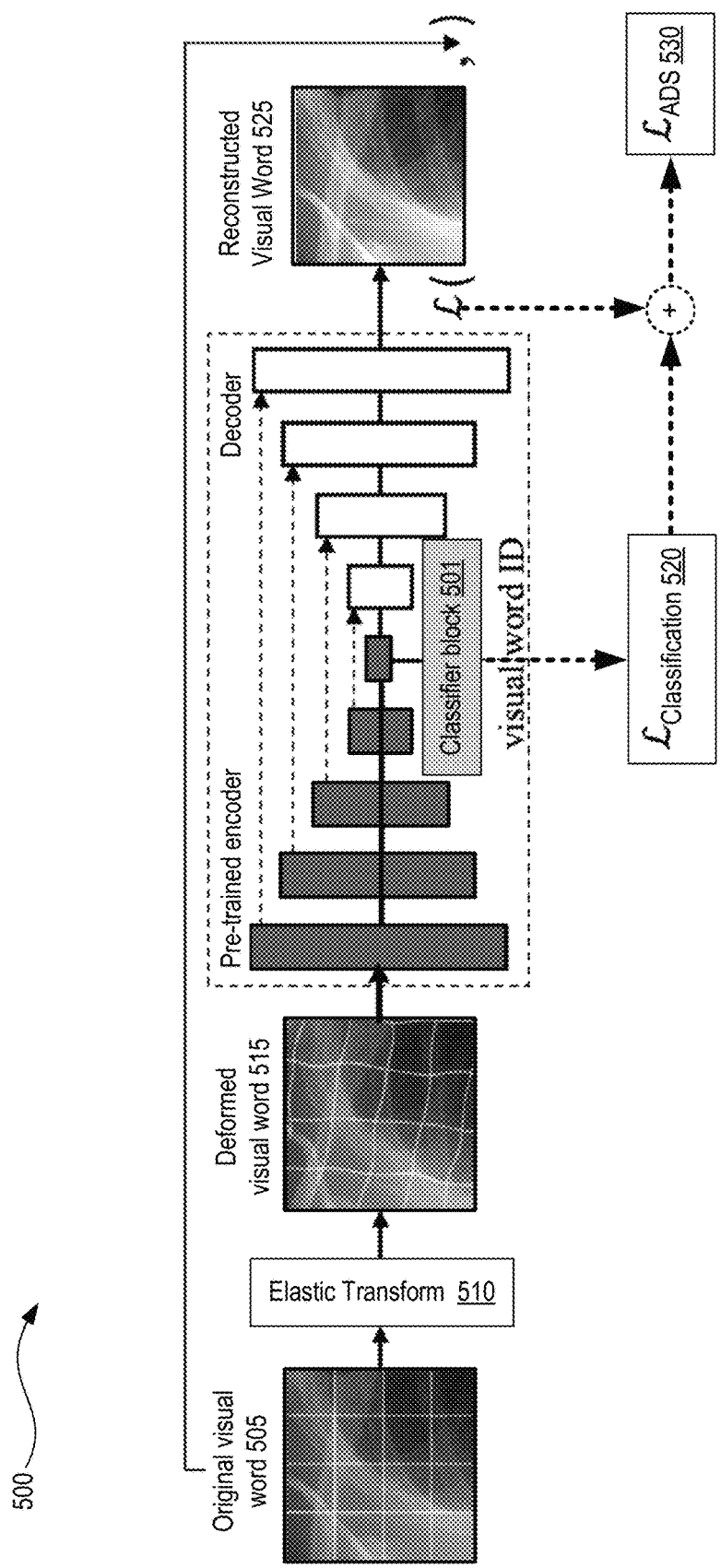
FIG. 5 depicts an exemplary representation of Anatomy-aware Dual-task Self-supervised (ADS) Learning in accordance with described embodiments.

The incoming dataset is labeled, however, the labels of the dataset are not utilized for the purpose of the proxy task. Rather, the labels of the dataset are only utilized for the target task. According to described embodiments, the dataset is divided into two parts (e.g., refer to table 2 below, showing "Part 1 without disease labels" and "Part 2 without disease labels"). As will be described in greater detail below, there are three separate proxy tasks. The part 1 dataset without labels is utilized by the first proxy task to train the Coordinate-based Visual Word (CVW) classifier. The part 2 dataset without labels is utilized by the second proxy task in which the first proxy network (e.g., the CVW classifier) is utilized by the second proxy task to improve the consistency between the visual words (e.g., image patches) as shown at FIG. 3, element 330. Next, having the more consistent visual words, the Anatomy-aware Visual Word (AVW) Learning model is trained as the second classifier as shown at FIG. 4, element 425. Next, the weight of the second proxy task is transferred to the third proxy task, as is shown by FIG. 5 at element 501 showing the "pre-trained encoder" in blue. Finally, the weights of the third proxy task (ADS encoder) are transferred to the target task and the network is fine-tuned for the purposes of the target task which utilizes the dataset with the labels.

For instance, according to certain embodiments, there are provided systems and methodologies for implementing transferable visual words beneficially combining the transfer learning capability of Convolutional neural networks (CNNs) with the unsupervised nature of Bag of Visual Words (BoVW) machine learning models for use with extracting visual words, thus resulting in the new and novel self-supervised method methodology referred to herein as transferable visual words or "TransVW," which is realized through the transfer of the learned representations from proxy CNN to the target CNN.

Transfer learnings from ImageNet machine learning models to medical images has become the de facto solution for a wide range of 2D medical imaging applications, with nearly all conventionally known methodologies are based on the transfer of learnings from pre-trained ImageNet models. The ImageNet project provides a large visual database designed for use in visual object recognition software research, with more than 14 million images having been hand-annotated in furtherance of the project to indicate what objects are pictured and in at least one million of the images, with many of the images further providing bounding boxes. ImageNet contains more than 20,000 categories with typical categories, such as "balloon" consisting of potentially several hundred images and an average of over five hundred images per node or category.

Unfortunately, self-supervised learning has been sparsely applied to the field of medical imaging with the few examples of self-supervising learning in a medical imaging context including (i) the predicting of 3D distances between two patches sampled from the same brain as a self-supervised task for brain area segmentation, re-colorization of grayscale endoscopic video frames for the segmentation of medical instruments from endoscopic video and (ii) the predicting of longitudinal relationships between MRI scans for a disc degeneration classification task, and (iii) pre-training a stack of de-noising auto-encoders to remove noise from sampled patches of brain image volumes for brain lesion detection and segmentation applications. Conventionally known approaches do not benefit from the consistent visual patterns for self-supervised learning as is possible with transferable visual words utilizing the methodologies as set forth herein.

Consider for instance, the medical condition and diagnosis of thorax disease. Since the release of ChestX-ray14, various approaches have been developed for thorax disease identification, with one such approach involving simultaneous disease classification and localization by leveraging both class information as well as limited location annotation, in which use of the location annotation improves the classification performance and also reduces the number of training images.

A multi-attention network for chest X-ray classification and localization has also been used with some limited success, in which there are three attention modules consisting of (i) a first module for cross-channel feature re-calibration, (ii) a second model to include both global and local information, and (iii) a third and final module to alleviate class imbalance problems.

Yet another approach applies a machine learning model which incorporates disease severity levels to use a curriculum learning principle in an attention-guided method to classify and localize the thorax diseases. The effect of different deep learning approaches on the performance of multi-label chest X-ray image classification, including the effect of transfer learning from ImageNet, network architecture, and using non-image features has also been investigated, and found that random splitting of the ChestX-ray14 dataset has a significant effect on the performance of the target task. A location aware dense network which utilizes high resolution images beside spatial information has been proposed for chest X-ray classification. Yet another approach involves a category-wise residual attention learning framework to consider the correlation among relevant diseases and mitigate the interference of uncorrelated diseases for chest X-ray classification.

Notably, however, all of the above approaches rely upon location annotations, attention modules or additional training data to improve chest X-ray classification and further rely upon fine-tuned pre-trained ImageNet models where such models are available.

While Convolutional Neural Networks (CNNs) and Bag of Visual Words (BoVW) machine learning models are often regarded as competing and incompatible methodologies, the improved techniques and methodologies described herein utilizing transferable visual words beneficially combine the transfer learning capabilities of Convolutional neural networks (CNNs) with the unsupervised nature of Bag of Visual Words (BoVW) machine learning models specifically to leverage the complementary strengths of the respective CNN and BoVW machine learning models.

Improving chest X-ray classification without using pre-trained ImageNet models and reconciling the opposing features of CNNs and BoVW to amplify their strengths has not yet been successfully demonstrated via conventionally available solutions. Annotating medical imaging is tedious and time consuming, and also demands costly, specialty-oriented knowledge and skills, which are not easily accessible. Furthermore, any misdiagnosis from failure to recognize or correctly identify anatomical structures and abnormalities may result in potentially devastating impacts on patient morbidity and mortality.

Training a CNN machine learning model requires a large number of training images but in doing so, it is possible for the learned features of the CNN to be transferred to other applications, including into the field and application of medical imaging. The sophisticated, recurrent anatomical structures in medical images are natural visual words (see FIG. 1A), which can be automatically extracted, serving as strong yet free supervision signals for CNNs to learn generalizable image representation via self-supervision, and the learned image representation can be transferred to application-specific target tasks. We have evaluated TransVW on NIH ChestX-ray14, a hospital-scale chest X-ray dataset, demonstrating that our TransVW outperforms all the state-of-the-art approaches, including those fine-tuning pre-trained ImageNet models This is an unprecedented achievement, given that our TransVW is self-supervised, requiring no expert annotation in pre-training, and heretofore, no method in self-supervised learning has outperformed pre-trained ImageNet models.

Embodiments of the invention therefore improve upon conventionally known image representation and learning techniques by advantageously integrating CNNs and BoVW to amplify their strengths, leading to more powerful solutions to applications, especially in medical imaging. Methodologies utilizing transferable visual words as described in detail below are based on the simple yet powerful observation that segments of sophisticated, consistent and recurrent anatomical structures in medical images are natural visual words or common anatomical patterns which can be automatically extracted, serving as strong yet free supervision signals for CNNs machine learning models to learn generalizable image representation via self-supervision. These learned image representations are then transferred to application-specific target tasks by distilling transferable features via self-supervised learning.

As will be described in greater detail below, embodiments utilizing the transfer of learned representations representing the identified visual words are configured to automatically extract visual words directly from images without requiring any clustering, with such embodiments then further integrating the BoVW machine learning model's unsupervised visual word extraction nature with the CNN machine learning model's transferable representation learning power.

More specifically, embodiments applied specifically to chest X-ray medical imaging analysis applies the transferable visual word extraction and learning via three primary operations, including (i) a Coordinate-based Visual Word (CVW) Learning as is illustrated below at FIG. 3, which operates by extracting a set of visual words based on fixed coordinates within chest X-ray images and trains a classifier, named CVW with these extracted visual word instances and their IDs as ground truth. Next, application of the transferable visual words methodology operates by (ii) using an Anatomy-aware Visual Word (AVW) Learning model as illustrated below at FIG. 4 to enhance the consistencies among extracted visual word instances with the trained CVW classifier. Lastly, application of the transferable visual words methodology operates by (iii) applying an Anatomy-aware Dual-task Self-supervised (ADS) Learning model as is illustrated at FIG. 5 below, which incorporates visual word classification with visual word restoration to further enhance the representation learning capability of transferable learned representations (e.g., also referred to as "weights" learned from the first CNN model) representing the identified TransVW.

Exemplary visual word instances include image patches (samples) extracted across different images for the same visual word. Naturally, instances of the same visual word exhibit great similarity and consistency in appearance. As each visual word has a unique identifier (e.g., a visual word ID), all instances of a visual word will therefore also share the same visual word ID. However, an unrefined extraction process may result in inconsistency in the appearance of visual word instances. Thus, application of the transferable visual words embodiments as described herein beneficially combines the transfer learning capability of CNNs with the unsupervised nature of BoVW in extracting visual words from X-ray images through a two-step scheme involving coordinate-based visual word (CVW) learning and anatomy-aware visual word (AVW) learning. Such a process therefore ensures consistency in the appearance of visual word instances, providing unprecedented improvements over the conventionally known methodologies, given that use of the transferable visual words methodologies set forth herein are self-supervised, requiring no expert annotation in pre-training. Simply stated, no conventionally known approach which applies self-supervised learning can outperform results provided by the techniques taught and claimed herein for thorax disease identification, including those which utilize pre-trained ImageNet models.

Use of the transferable visual words therefore thus reduces annotation efforts in the medical field with exceptional performance that outperforms even the most state of the art approaches, including models of the same architecture trained from scratch and fine-tuned pre-trained ImageNet models. These improvements are expected to result in improved patient health and saved lives, as well as improving image representation in a wide array of technical fields, especially medical imaging. Stated differently, the methodologies described herein provide solutions to improving image representation systems via self-supervised, generalizable and transferable image representation of objects that are subject to unknown, ever-changing, and varying parameters, conditions, and characteristics, such as pathology and anatomical nuances in the human body.

In the following description, numerous specific details are set forth such as examples of specific systems, languages, components, etc., in order to provide a thorough understanding of the various embodiments. It will be apparent, however, to one skilled in the art that these specific details need not be employed to practice the embodiments disclosed herein. In other instances, well known materials or methods have not been described in detail in order to avoid unnecessarily obscuring the disclosed embodiments.

In addition to various hardware components depicted in the figures and described herein, embodiments further include various operations which are described below. The operations described in accordance with such embodiments may be performed by hardware components or may be embodied in machine-executable instructions, which may be used to cause a specialized and special-purpose processor having been programmed with the instructions to perform the operations described herein. Alternatively, the operations may be performed by a combination of hardware and software. In such a way, the embodiments of the invention provide a technical solution to a technical problem.

Embodiments also relate to an apparatus for performing the operations disclosed herein. This apparatus may be specially constructed for the required purposes, or it may be a special purpose computer selectively activated or reconfigured by a computer program stored in the computer. Such a computer program may be stored in a computer readable storage medium, such as, but not limited to, any type of disk including floppy disks, optical disks, CD-ROMs, and magnetic-optical disks, read-only memories (ROMs), random access memories (RAMs), EPROMs, EEPROMs, magnetic or optical cards, or any type of media suitable for storing electronic instructions, each coupled to a computer system bus.

The algorithms and displays presented herein are not inherently related to any particular computer or other apparatus. Various customizable and special purpose systems may be used with programs in accordance with the teachings herein, or it may prove convenient to construct more specialized apparatus to perform the required method steps. The required structure for a variety of these systems will appear as set forth in the description below. In addition, embodiments are not described with reference to any particular programming language. It will be appreciated that a variety of programming languages may be used to implement the teachings of the embodiments as described herein.

Embodiments may be provided as a computer program product, or software, that may include a machine-readable medium having stored thereon instructions, which may be used to program a computer system (or other electronic devices) to perform a process according to the disclosed embodiments. A machine-readable medium includes any mechanism for storing or transmitting information in a form readable by a machine (e.g., a computer). For example, a machine-readable (e.g., computer-readable) medium includes a machine (e.g., a computer) readable storage medium (e.g., read only memory ("ROM"), random access memory ("RAM"), magnetic disk storage media, optical storage media, flash memory devices, etc.), a machine (e.g., computer) readable transmission medium (electrical, optical, acoustical), etc.

Any of the disclosed embodiments may be used alone or together with one another in any combination. Although various embodiments may have been partially motivated by deficiencies with conventional techniques and approaches, some of which are described or alluded to within the specification, the embodiments need not necessarily address or solve any of these deficiencies, but rather, may address only some of the deficiencies, address none of the deficiencies, or be directed toward different deficiencies and problems which are not directly discussed.

In addition to various hardware components depicted in the figures and described herein, embodiments further include various operations which are described below. The operations described in accordance with such embodiments may be performed by hardware components or may be embodied in machine-executable instructions, which may be used to cause a special-purpose processor programmed with the instructions to perform the operations. Alternatively, the operations may be performed by a combination of hardware and software, including software instructions that perform the operations described herein via memory and one or more processors of a computing platform.

Medical imaging protocols typically focus on particular parts of the human anatomy for dedicated clinical purposes, resulting in images of similar anatomy—the lungs in the case of chest X-rays, which understandably exhibit complex, albeit consistent and recurring patterns across acquired images. The medical imaging analysis techniques as described herein are therefore well-suited for a specially built computing system having been appropriately configured to carry out and implement the new and novel methodologies for using visual words as described herein.

Figure 1A:
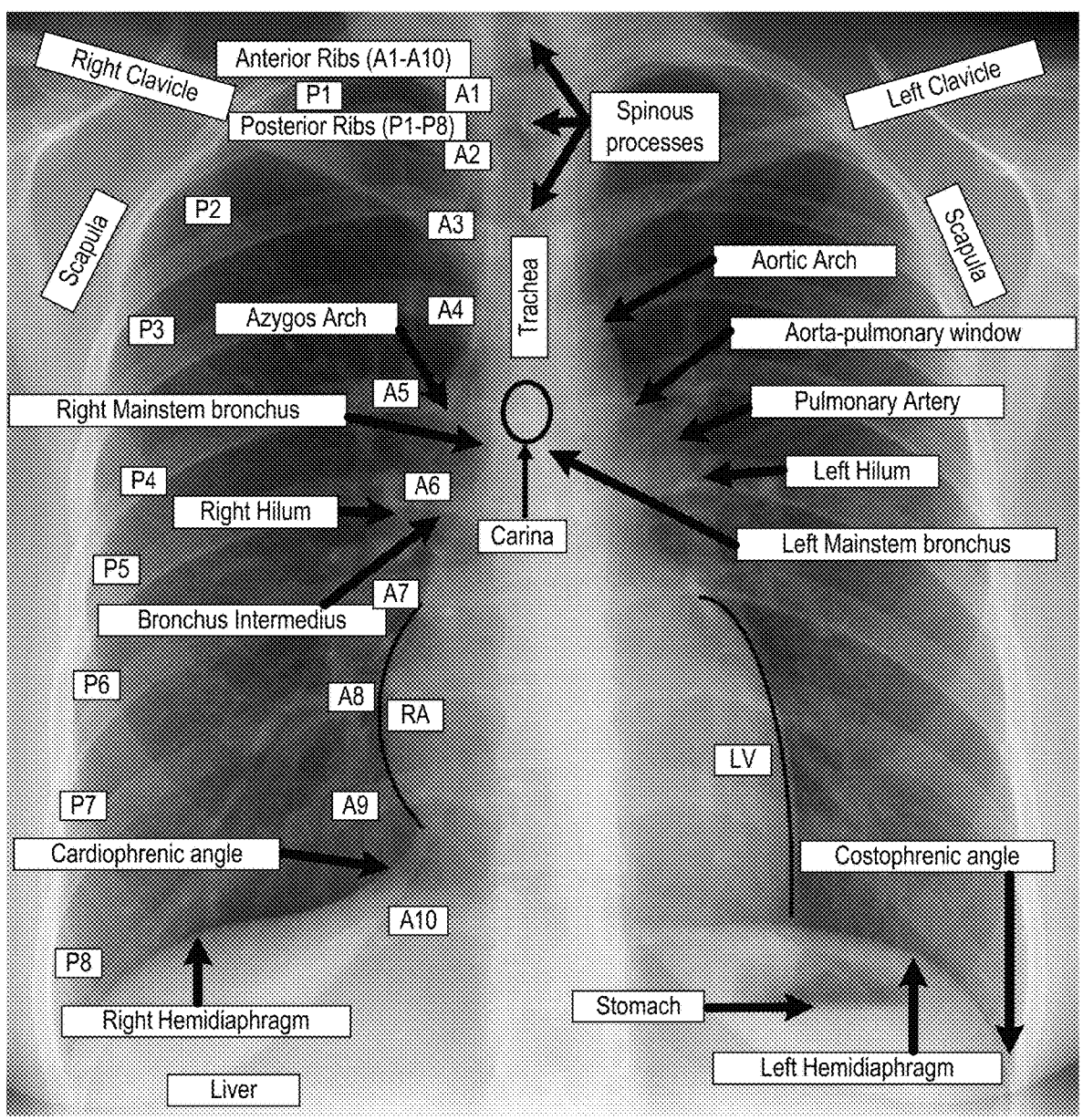
FIG. 1A depicts an exemplary visualization of the lungs in an annotated chest X-ray in accordance with described embodiments.

FIG. 1A depicts an exemplary visualization of the lungs in an annotated chest X-ray in accordance with described embodiments.

The sophisticated anatomy of the lungs yields consistent and recurring patterns and anatomical structures across X-rays, referred to herein as chest X-ray visual words. According to described embodiments, it is these visual words which are automatically extracted and thus serve as strong yet free supervision signals for CNNs to learn generalizable image representations via self-supervision. The learned image representations are then transferred to application-specific target tasks.

This solution is referred to herein as TransVW or "transferable visual words" because its annotation efficiency stems from two sources: the power of transfer learning with CNNs and the unsupervised property of visual word extraction with bags of visual words (BoVW).

The NIH ChestX-ray14 dataset was specifically utilized for the evaluation described below. The NIH ChestX-ray14 is a hospital-scale chest X-ray dataset. The evaluation described below demonstrates that (1) relative to training from scratch and ImageNet-based transfer learning, TransVW reduces the annotation efforts by 75% and 12%, respectively (refer also to FIG. 7A below). The evaluation further demonstrates that (2) when the full annotation of the official training set is utilized, the TransVW methodology significantly accelerates the convergence speed in comparison with training from scratch and ImageNet-based transfer learning (see also FIG. 7B below). The evaluation still further demonstrates that: (3) the TransVW methodology achieves the best average AUC (Area under the ROC Curve) on all 14 diseases, the best individual AUC scores on 10 diseases, and the second best individual AUC scores on 3 diseases (refer to Table 1 below). These are exceptional achievements that have not been attained by any prior known methodology.

Figure 6:
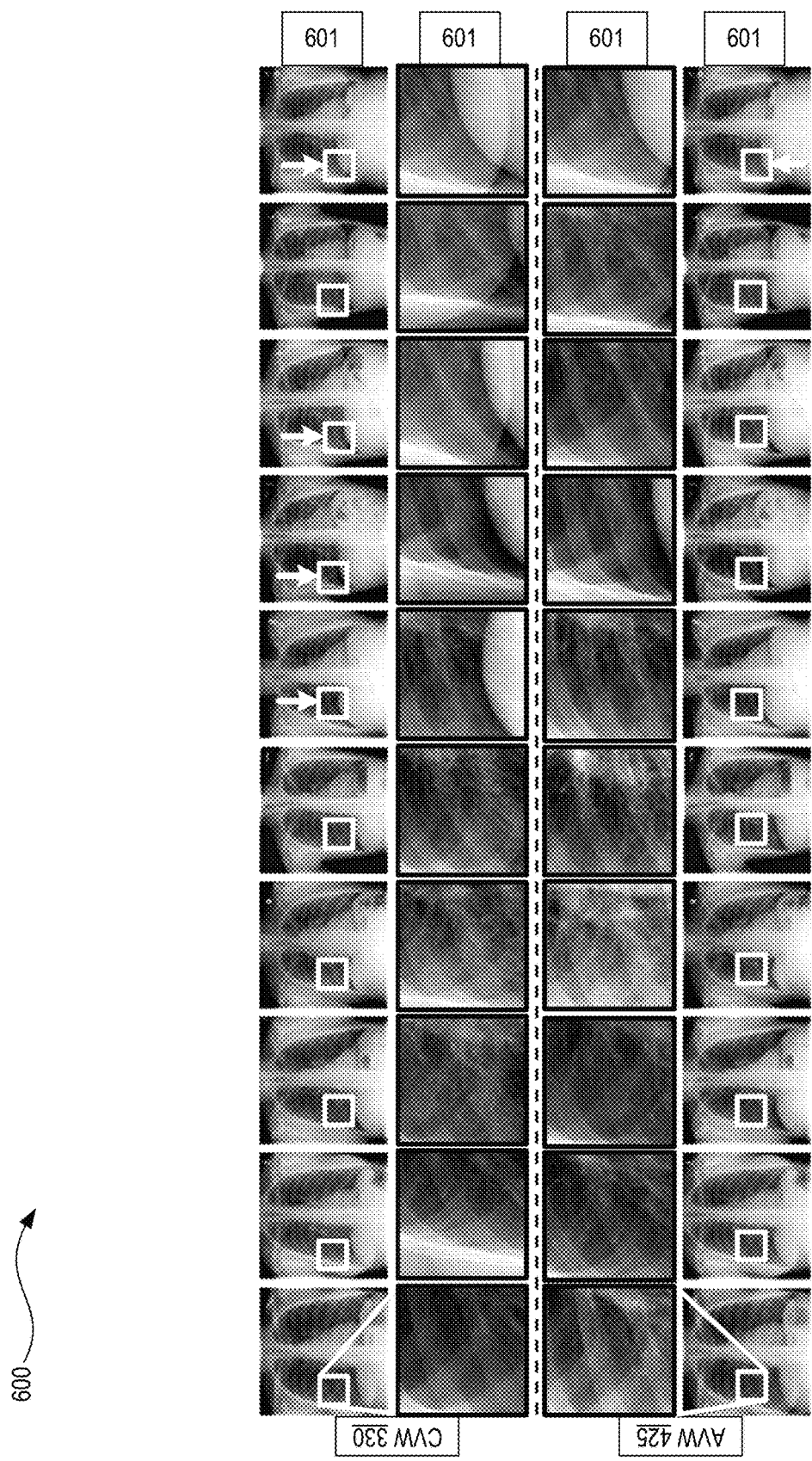
FIG. 6 depicts an exemplary visual comparison of localizing ten different visual word instances by CVW classifier (top row 601), AVW classifier (bottom row 604) in the same test images, as well as zoomed in views of CVW localization (second row 602) and AVW localization (third row 603), in accordance with described embodiments.

Further still, practice of the TransVW methodology provides the additional contributions and improvements over conventional methodologies: Firstly, the TransVW methodology leverages the entirely new idea that the sophisticated and recurrent anatomical structures in medical images are natural visual words, which can be automatically extracted, serving as strong yet free supervision signals for CNNs to learn common anatomical representation via self-supervision. Additionally, in support of the TransVW methodology, a two-step scheme has been devised to automatically extract visual words directly from X-ray images, thus ensuring their consistency in appearance (as is illustrated in FIG. 6). Still further, a U-Net-like architecture has been designed in support of the TransVW methodology to enhance TransVW's representation learning capability by simultaneous classification and restoration of visual words as will be described in greater detail below. Still further, statistical analysis conducted demonstrates that the TransVW methodology outperforms models of the same architecture trained from scratch as well as fine-tuned from pre-trained ImageNet models. Moreover, the TransVW methodology is evaluated based on the official split of NIH ChestX-ray14, a hospital-scale chest X-ray dataset, demonstrating that our TransVW outperforms all the State-Of-The-Art approaches, including those which fine-tune pre-trained ImageNet models. Finally, use of the TransVW methodology has been further demonstrated through the evaluation to reduce annotation efforts by 75% relative to training a model from scratch and by 12% relative to fine-tuning a pre-trained ImageNet model (see FIG. 7A).

FIGS. 1B, 1C, 1D, and 1E depict alternative exemplary visualizations of the lungs in an annotated chest X-ray in accordance with described embodiments.

As shown in Table 1 below, transferable visual words (TransVW) provides a self-supervised learning method without expert annotation in pre-training which achieves the unprecedented outcome of outperforming all state-of-the-art approaches (SOTA) when applied to the NIH ChestX-ray14 hospital-scale chest X-ray dataset. Most conventionally known methodologies are pre-trained ImageNet models which are models pre-trained with a large number of labeled images. The TransVW model yields superior performance over all existing state-of-the art Chest-ray 14 classification methods. In addition to achieving the best average over fourteen pathologies, TransVW achieves the best performance on ten pathologies compared to any previously known method.

Table 1 compares the State-Of-The-Art (SOTA) methods on an official split of ChestX-ray14 shows that the described TransVW methodology achieves the best mean performance over all diseases ('Mean' column at the far right) and the best performance on ten diseases, delivering remarkable performance over prior known techniques given that no self-supervised methods have thus far outperformed pre-trained ImageNet models. The best and second best performance on each disease is in bold and underlined, respectively. The columns labeled "Arch", "Init", "RN", and "DN" stand for the architecture, initialization, ResNet, and DenseNet, respectively.

The results in Table 1 demonstrate that fine-tuning from the TransVW model yields superior performance over all existing state-of-the-art ChestX-ray14 classification methods. In addition to achieving the best average over fourteen pathologies, TransVW achieves the best performance on ten pathologies. Also, in "Nodule", "Emphysema", and "Pleural Thickening", the AUC improves more than 2% in comparison to the Guan and Huang 2018 method, which had the best performance among all of the previously known methods tested. The embodiments disclosed herein thus pioneer a self-supervised approach for X-Ray modality to achieve the best performance in multi-label chest X-ray image classification over previous methods fine-tuned the pre-trained ImageNet models, with improvements to the new methodologies specifically relying upon transferable visual words obtained from large-scale unlabeled data and thus require no expert annotation effort. In such a way, not only is performance improved, but overhead and cost is reduced through application and practice of the disclosed methodologies.

Self-supervised learning in computer vision: Self-supervised learning research has recently received a great attention in computer vision and several approaches have been proposed, however, as is shown in Table 4B, these approaches generally offer little benefits to chest X-rays, because the dense anatomical patterns (visual words) in X-rays seem to make them learn trivial solutions, leading to poor performance. Therefore, the TransVW methodology was developed to overcome these shortcomings present in prior known techniques (see FIG. 1A).

Transfer learning and self-supervised learning in medical imaging: Transfer learning from ImageNet to medical images has become the de facto solution for a wide range of 2D medical imaging applications. As evidenced in Table 1, nearly all the State-Of-The-Art methods are based on transfer learning from pre-trained ImageNet models. Self-supervised learning is sparsely applied in medical imaging. Prior techniques considered use of a 3D distance between two patches sampled from the same brain as a self-supervised task for the brain area segmentation and use of re-colorization of the grayscale endoscopic video frames for the segmentation of medical instruments from endoscopic video, as well as the use of a longitudinal relationship between MRI scans for the disc degeneration classification task, and a stack of denoising auto-encoders having been pre-trained to remove noise from sampled patches of the brain image volumes for the brain lesion detection and segmentation applications. However, none of these approaches exploited the consistent visual patterns for self-supervised learning as is done with the TransVW methodology described herein. What makes the TransVW methodology even more outstanding is that it uses no expert annotation in pre-training, yet outperforms the ImageNet-based models, which are pre-trained with a large number of labeled images (see Table 3).

Figure 2:
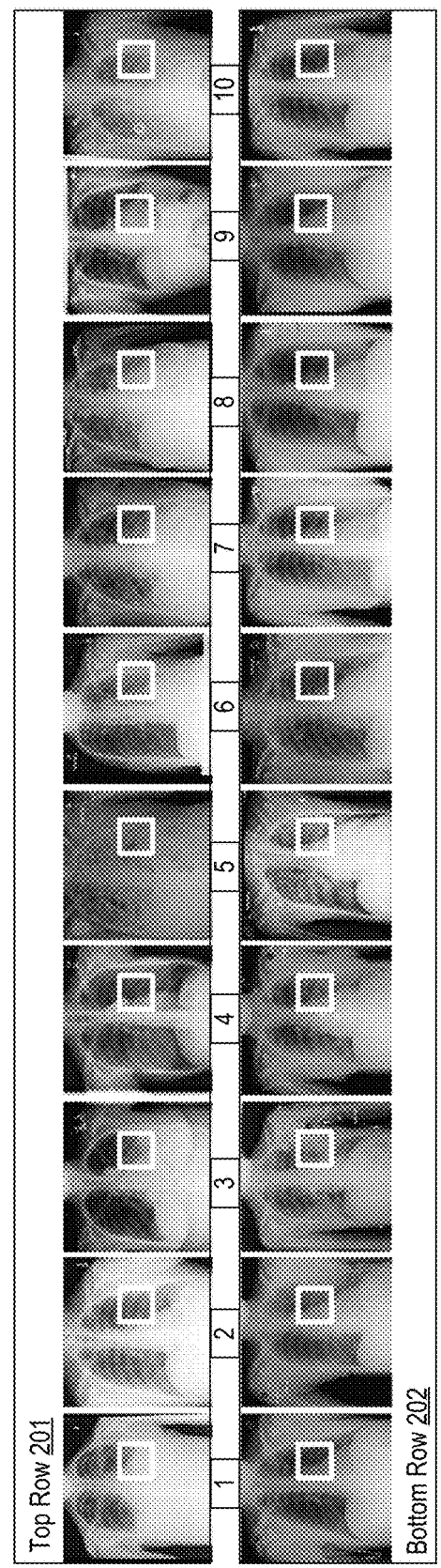
FIG. 2 depicts an exemplary visual comparison of the large variation of visual word instances when utilizing a fixed coordinate across images (top row 201) as compared to enhanced consistency with utilizing topmost similar X-rays (bottom row 202) in accordance with described embodiments.

FIG. 2 depicts an exemplary visual comparison of the large variation of visual word instances when utilizing a fixed coordinate across images (top row 201) as compared to enhanced consistency with utilizing topmost similar X-rays (bottom row 202) in accordance with described embodiments.

Even with the great similarities among chest X-rays, naively extracting instances of a visual word at a fixed coordinate across all images (the top row of FIG. 2) yields a large variation among the instances in terms of covered anatomical structures; referring to the expert annotation in FIG. 1, four instances (3, 4, 7, and 8) overlap with the "left hilum" and six instances (3, 4, 6, 7, 8, and 9) cover a portion of "LV contour". To enhance the consistency among the instances, for a given X-ray (the left most image in the bottom row of FIG. 2), the TransVW methodology identifies its corresponding topmost similar X-rays (the bottom row of FIG. 2) from the training dataset, before extracting instances of a visual word at a fixed coordinate, leading to the same anatomical part in the most instances of a visual word. All instances except instance 10 are centered on the "left hilum". Additionally, all instances, except instance 6, catch a portion or most of "LV contour". The TransVW methodology then further enhances the consistency among visual word instances through the AVW learning process, which is described below in greater detail with reference to FIG. 6.

Multi-label chest X-ray (CXR) classification on the ChestX-ray14 dataset: Since the release of the ChestX-ray14 dataset, various approaches have been developed for thorax disease identification. For example, prior techniques performed disease classification and localization simultaneously by leveraging both class information as well as limited location annotation, demonstrating that utilizing the location annotation improves the classification performance and also reduces the number of training images. In other prior known techniques, a multi-attention network for chest X-ray classification and localization was utilized, in which the network consisted of three attention modules: (i) the first module being used for cross-channel feature recalibration, (ii) a second module used to include both global and local information, and (iii) a third module which alleviates class imbalance problems. Still other techniques incorporated a disease severity level to utilize the curriculum learning principle in an attention-guided method to classify and localize the thorax diseases. The effect of different deep learning approaches on the performance of multi-label chest X-ray image classification has also been investigated, including the effect of transfer learning from ImageNet, network architecture, and using non-image features. It has been shown that random splitting of the ChestX-ray14 dataset has a significant effect on the performance of the target task. Moreover, a location aware dense network which utilizes the high resolution images besides the spatial information has been proposed for CXR classification. A category-wise residual attention learning framework has also been proposed to consider the correlation among relevant diseases and mitigate the interference of the uncorrelated diseases for CXR classification. Generally speaking, all of the previously known approaches used location annotations, attention modules, or additional training data to improve the CXR classification performance. With rare exception, all existing methods utilize fine-tuned pre-trained ImageNet models. In contrast, the TransVW methodology purposefully exploits common anatomical patterns (visual words) of X-ray images to distill transferable features via self-supervised learning, requiring no expert annotation in pre-training, resulting in dramatic out-performance of thorax disease identification over prior known methods (see Table 1).

Despite the similar anatomy of medical images, several factors, such as the position of the patient's body, and the angle at which the image is taken, affects the visual word extraction process. In fact, the instances of the same visual word can be located at different coordinates in different images. Extracting consistent instances of visual words across all images is a challenge. A naive approach would be selecting a specific coordinate in different images and then extracting instances of the visual word around that specific coordinate in all images. However, due to the aforementioned factors leading to the different coordinates of the instances of the same visual word in different images, this hasty approach would yield an extensive variation among the anatomical patterns covered by visual word instances.

For example, at the top row, there are some inconsistencies amongst the images, despite each instance being the same anatomical element within the chest X-ray. Conversely, in the bottom row, extracting patches at the same coordinate yields much more consistent patterns, with every one of the bottom row images appearing to be visually consistent with the left most first image instance on the bottom row. By selecting these improved consistency images it is then possible to further improve the target disease classification accuracy. These more consistent images patches within the yellow boxes on the bottom row therefore contain the same visual pattern and are shown at the same part of the chest same coordinate in each yellow box, despite being selected from different images. This is accomplished by the image matching process described in greater detail below.

Even with the great similarities among chest X-rays, naively extracting instances of a visual word at a fixed coordinate across all images (the top row) yields a large variation among the instances in terms of covered anatomical structures. To enhance the consistency among the instances, for a given X-ray (the left most image in the bottom row), the topmost similar X-ray is identified (the bottom row) from the training dataset, before extracting instances of a visual word at a fixed coordinate, leading to the same anatomical part in the most instances of a visual word.

Instances of a visual word are image patches (samples) for the same visual word across different images. As further demonstrated in FIG. 2, even with the great similarities among chest X-rays, naively extracting instances of a visual word at a fixed coordinate across all images coordinate across all images (FIG. 2, top row 201) would yield a large variation among the instances in terms of covered anatomical structures. Comparing to the expert annotation in FIG. 1A, four instances in FIG. 2 (top row 201 3, 4, 7, and 8) overlap with the "left hilum" and six instances in FIG. 2 (top row 201 3, 4, 6, 7, 8, and 9) cover a portion of "LV contour."

To enhance the consistency among the instances, for a given X-ray, such as the leftmost X-ray in bottom row 202 of FIG. 2), the most similar X-rays (the other X-rays in the bottom row 202 of FIG. 2) are identified from the training dataset before extracting instances of a visual word at a fixed coordinate. This leads to the same anatomical part in the most instances of a visual word. All instances, except Instance 10 of FIG. 2, bottom row, are centered on the "left hilum." Additionally, all instances, except instance 6 of FIG. 2, bottom row, catch a portion or most of "LV contour". The consistency among visual word instances is further enhanced through Anatomy-aware visual word (AVW) learning (see FIG. 6).

Based on the Table 2, the official training data has been divided into two parts: Part 1 and Part 2. The training images without disease labels in Part 1 are used in "coordinate-based visual word (CVW) learning" for training the CVW classifier to enhance consistency of visual word instances, while the training images without disease labels in Part 2 are used in "anatomy-aware visual word (AVW) learning" for training the AVW classifier to learn consistent visual words as well as in "anatomy-aware dual-task self-supervised learning" for training the ADS network to improve representation learning. For the target task of thorax disease classification, the ADS encoder is fine-tuned with all the official training data with their disease labels. The 'w' and 'w/o' refer to with and without, respectively. As previously mentioned, Table 1 uses classified thorax disease to compare the performance of various architectures.

The CVW classifier is designed to yield more consistent visual words, as shown by FIG. 3. The consistent visual word is then utilized by the AVW classifier as shown by FIG. 4 to provide another pretext or proxy task which seeks to learn the most consistent visual word and thus provides as output the most consistent visual word for each M class. Finally via the ADS self-supervised learning process as shown by FIG. 5, the weights of ADS encoder is called TransVW and are transferred to the target task. In the target task, the pre-trained model is fine-tuned to diagnose diseases within never before seen medical X-ray images.

FIG. 3 depicts use and application of a Coordinate-based Visual Word (CVW) classifier in accordance with described embodiments.

To extract the instances of visual word i, from Part 1 of the training set, the described methodology, operation 310 (a) first randomly selects an X-ray image as a reference image, operation 315 (b) uses an image registration technique to find the N most similar images to the reference image, and operation 320 (c) extracts patches at the ith randomly-generated unique coordinate across all images found in operation 315 (b). These extracted patches are referred to as the instances of the visual word with visual word ID i. Operations 315 (b) and 320 (c) together aim to ensure that the instances of each visual word across all images roughly cover the same anatomical part (referring to FIG. 2). After extracting instances for all M visual words, at operation 315 (d), a network is then trained with the prepared data to classify these instances into M classes with their visual word IDs as ground truth. The trained classifier is referred to as the CVW classifier 330. Details of the coordinate-based visual word extraction procedure is summarized in Algorithm 1 as depicted in detail at FIG. 9A.

With reference again to FIG. 1A, it may be observed within the chest X-ray that some patterns within the chest X-ray image are recurring. For instance, note that the annotations for the variously labeled elements, such as anterior ribs, Right Hilum, Right Clavicle, etc.

Because these patterns within the chest X-ray image are known to be recurring, it is possible therefore to apply a 3-step machine learning methodology to train a neural network through a self-supervised learning methodology. Once trained, the neural network is then able to identify elements within previously unseen chest X-ray images and diagnose disease within the previously unseen chest X-ray images with a higher degree of accuracy and confidence than is possible with prior known methodologies.

Referring again to FIG. 3, step 1 of the three-step methodology begins with the receipt or input of a dataset. As shown here, ChestXRay14 is presented as the dataset at element 305. Continuing with step 1, the dataset is next divided into two parts (e.g., part 1 and part 2), and from the first part of the dataset, a random X-ray image is selected for use. Next, using image registration technique similar images from the dataset are identified which match the previously selected random X-ray image, as depicted at block 310.

Continuing with step 1 of the three-step methodology, processing next operates to choose random coordinates from the similar images identified within the dataset and from those random coordinates for each of the similar images (e.g., refer to block 315), image patches are extracted at those random coordinates, with these random patches being referred to as "visual words," as depicted at block 320 having the yellow boxes identifying the extracted patches at the random coordinates, thus identifying the "visual words."

Finally, concluding the sub-operations of step 1 of the three-step methodology, the CVW classifier identified at element 330 attempts to classify the visual words corresponding to the extracted patches referenced above, with the CVW classifier classifying the available visual words into M different classes.

Processing then advances to step 2 of the three-step methodology, which is described in greater detail below with regard to the elements set forth at FIG. 4.

FIG. 4 depicts use and application of an anatomy-aware visual word (AVW) classifier in accordance with described embodiments.

Inevitably, there are some inconsistencies among instances of a visual word extracted from the CVW step, since they are extracted based on a fixed coordinate across all images. Therefore, to ensure the consistency of visual word instances, operation 410 (a) slides a window on the entire image to generate patches as input to the pre-trained CVW classifier 330 which then, at operation 415 (b) localizes the M visual words in each image in Part 2 of the training images. For each visual word, operation 420 (c) selects the top K most confident instances among all images in Part 2 of the training images. Finally, operation 425 (d) trains a classifier to classify the visual words into M classes. The trained classifier is referred to as the AVW classifier 425.

Due to the drawbacks of using existing image matching algorithms in the medical imaging domain, some of the found images in the coordinate-based visual word (CVW) extraction procedure may not be similar to the reference image utilized at step 1 above for the purposes of identifying the similar images in the dataset. Thus, extracting instances of a visual word from a specific coordinate across all found images identified as being similar may produce inconsistent instances within each class M of visual words given that the visual words are extracted based on a fixed coordinate across all images.

Therefore, unlike step 1 of the three-step methodology above utilizing the CVW classifier, during which instances of a visual word are extracted based on a specific coordinate, during step 2 of the three-step methodology utilizing the AVW classifier, the instances of the same visual word are now extracted utilizing different coordinates for the different images, and yet, correspond to and thus cover or represent the same part of the anatomical structure from each given X-ray image. In an effort to produce more robust anatomical features, the second classifier utilized at step 2 of the three-step methodology, specifically the AVW classifier, is trained to classify new and more consistent visual words into the M classes. Refer to the details of the anatomy-aware visual word extraction procedure as provided at Algorithm 2 as depicted in detail at FIG. 9B.

To ensure the consistency of visual word instances, processing at step 2 of the three-step methodology therefore slides a window on the entire image to generate patches as inputs to the CVW classifier so as to localize the M classes of visual words in each image in the second part (e.g., Part 2) of the training images dataset. For each visual word, processing selects the top K most confident instances among all images in part 2 of the training images dataset and then concludes by training the AVW classifier to classify the visual words into the M classes.

Therefore, step 2 of the three-step methodology includes at least the following sub-operations: Firstly, utilizing the second part of the chest X-ray images dataset (refer to element 405 identifying ChestX-Ray14 Part 2), an image is selected and processing slides a window over each of the images to find and identify the M visual words in each respective image (refer to element 410 depicting the sliding window over a respective chest X-ray image from the second part of the chest X-ray dataset). Next, through the sliding window operation at element 410 processing identifies the patches corresponding to the visual words for the various M classes and passes those identified patches to the CVW classifier to classify the identified patches into the M classes as shown at element 410. Next, processing of step 2 of the three-step methodology continues by selecting the visual words having the greatest confidence based on which of the patches have the most consistent output from the CVW classifier at element 410. For instance, it may be observed at element 415 that the image patches are less consistent on the top row than the image patches on the top row of element 420. Therefore, the image patches at element 420 will be selected based on those image patches being more consistent and thus having a higher quantifiable confidence score. For example, on the top row of element 415, while the same portion of the chest is represented, some of the image patches are off-set, being slightly forward or backward, and thus the same portion of the chest appears in a slightly different portion of the respective image patch. Conversely, on the top row of element 420, the same portion of the chest is again represented, but unlike the top row of element 415, the image patches at element 420 depict not only the same portion of the chest in each image but additionally represent the same portion of the chest at the same position within the respective image patches, and thus, the top row at element 420 presents the K most confident instances from each M class, with processing selecting this most confident and consistent group.

Similarly, although the image patches at the bottom of element 415 show the same portion of the chest, the image patches at the bottom of element 420 are more consistent because those same portions of the chest are actually positioned at the same location within the various images and thus have a greater accuracy based on their higher degree of consistency, and thus correspond to a greater quantifiable confidence score. Therefore, similar to the top row, the image patches from the bottom row of element 420 will be selected as the most confident instance of visual word M. Although all of the image patches shown at the top row of element 415 and 420 correspond to one M class, it is the most consistent instances which are selected based on their higher degree of consistency and thus greater confidence score, with the confidence score representing the degree of consistency being provided as an output by the CVW classifier as depicted at element 410, thus permitting the select of the most consistent instances from every one of the M classes of visual words.

Finally, processing of step 2 of the three-step methodology concludes by training a different Convolutional Neural Network (CNN) model and specifically training the Anatomy-aware Visual Word (AVW) as depicted at element 425 utilizing the selected K most confident instances from each M class to classify the extracted visual words into M classes at the AVW classifier. By training the AVW classifier utilizing the more consistent visual words it is possible to attain a greater degree of accuracy for diagnosis of diseases (e.g., refer to the accuracies as presented at Table 1).

The three steps of the methodology, and specifically processing for step 3 of the three-step methodology is next described with reference to FIG. 5 below in which the output of the AVW classifier is utilized as part of a self-supervised machine learning process.

FIG. 5 depicts an exemplary representation of Anatomy-aware Dual-task Self-supervised (ADS) Learning in accordance with described embodiments.

Anatomy-aware dual-task self-supervised learning: To further improve the representation learning capability of TransVW, visual word classification and restoration tasks are consolidated to introduce a novel Anatomy-aware Dual-task Self-supervised (ADS) Learning network. For example, a U-Net-like network with the AVW classifier embedded as its encoder for visual word classification and restoration simultaneously (dual-task) is trained to improve representational learning. The ADS network has one input, an instance of a visual word which is deformed by elastic transformation, and two outputs: (i) a visual word ID and (ii) a reconstructed visual word instance based on the deformed visual word. Each input visual word instance is deformed using elastic transformation and the deformed visual word instance is then passed to a dual-task learner network. Elastic transformation is a spatial-level deformation which has been used extensively as an effective data augmentation technique in medical imaging. However, for the first time, the embodiments disclosed herein utilize elastic transformation as a self-supervised image restoration task to learn the context of images. In fact, incorporating elastic transformation in visual word classification enhances the representation learning in two ways. First, in terms of the classification task, the elastic transformation acts as data augmentation that helps the classifier to learn more robust representations. Second, in terms of the image restoration task, the model learns the shape of objects within the visual words as well as the relative appearance of structures within them.

The gridlines on the original and deformed visual word instance illustrate the effect of elastic transformation on the visual word.

The output of the classification and restoration heads are the visual word ID and reconstructed visual word instance, respectively. The encoder in the trained network is referred to as the TransVW. Fine-tuning the TransVW outperforms the SOTA methods on NIH ChestX-ray14 classification (see Table 1).

Incorporating elastic transformation in visual word classification enhances representation learning in two ways. First, in terms of the classification task, the elastic transformation acts as data augmentation that helps the classifier to learn more robust representations. Second, in terms of image restoration tasks, the model learns the shape of objects within the visual words as well as the relative appearance of structures within them.

Since the last layers of a classifier network learn the task specific features, a classification block is added, consisting of two convolution and two fully connected layers, after the bottleneck layer of the encoder of an encoder-decoder architecture to use only the encoder layers, which contain generic features, in the target task. We initialize the encoder with the pre-trained AVW model. Finally, we train the network for visual words classification and restoration tasks jointly.

Therefore, processing via step 3 of the three-step methodology includes at least the following sub-operations: First, each of the visual words which were extracted at step 2 of the three-step methodology as described above are now represented at element 505. Each of the visual words (element 505) are then subjected to an elastic transformation process at element 510, thus producing the deformed visual words at element 515. The transformation applied distorts and deforms the original visual words as may be observed at element 515 in which the same image from element 505 is shown, albeit in a deformed format. Notably, the grid lines are no longer straight and perpendicular to one another, but rather, the grid lines and indeed the image itself within element 515 is now distorted.

The sub-operation processing of step 3 of the three-step methodology then continues at element 520 in which the blue portion at element 520 depicts the pre-trained encoder corresponding to the AVW classifier described above, which is depicted at element 425 at FIG. 4. The deformed visual words from element 515 are input into the pre-trained encoder at element 520 are next re-constructed via the Convolutional Neural Network (CNN) model represented at element 520, thus, outputting the reconstructed visual word at element 525 from the CNN model at element 520 having received the deformed visual word at element 515 as its input. In such a way, the original visual word image at element 505 is restored to its original form as depicted at element 525, notwithstanding having been deformed via the elastic transformation processing at element 510.

In such a way, the self-supervised learning methodology is realized through the processing of the three-step methodology described above, which then permits for the transfer of learned weights from the pre-trained encoder at element 520 to a target CNN model which is fine-tuned to be capable of performing identification of X-ray image elements and diagnosis of diseases within such X-ray images for never before seen X-ray images which are not part of any training dataset. For instance, utilizing such a trained CNN model, it is possible to diagnose disease within chest X-ray images for a medical patient and realize higher levels diagnosis accuracy than is possible with any prior known technique.

The ADS network is trained using a joint loss function consisting of categorical cross entropy and L2 norm distance as the loss functions of classification and image restoration tasks, respectively, which is defined below via equation 1, as follows:

$$\mathcal{L}_{ADS} = \frac{1}{T}\sum_{b=1}^{T} \alpha\left(-Y_b \log \hat{Y}_b\right) + \beta\left(\|X_b - \hat{X}_b\|_2\right) \quad \text{Equation 1}$$

where T is the batch size; $Y_b$, and $\hat{Y}_b$ denote the classification one hot ground truth, and predicted probabilities of $b^{th}$ sample, respectively. $X_b$, and $\hat{X}_b$ denote the reconstruction ground truth and reconstructed output of $b^{th}$ sample, respectively and further where a and p are the regularization parameters.

Weights of the encoder of ADS network are transferred to the target CNN, which is a CNN model, representing all of the information about the visual words of the X-ray images and because the CNN model which performs the "target task" is also a CNN, it is simple to transfer the weights from the encoder of ADS network to the CNN model which performs the target task so as to provide as its output a more accurate prediction of disease diagnoses within never before seen medical images after the second CNN network is fine-tuned with labeled data to perform the target task.

The self-supervised learning approach described herein therefore enables training of CNN models utilizing images which do not already have labels applied to them. For instance, the methodology may be utilized for medical images or general images which require classification and yet lack a large labeled dataset.

The training of the CNN model may be described as a "proxy task," in which the recurring patterns inside of the medical X-ray images (e.g., showing the heart, the ribs, etc.) as a supervision signal for use in training a CNN model. After the CNN network is trained via the proxy task using a self-supervised process, the weights from the CNN model trained via the proxy task are then transferred to another CNN network called a "target task," utilizing a "transfer learning" process, which transfers the weights of the CNN network trained utilizing self-supervision to a CNN network, in which the target task is a supervised classification task which benefits from improved performance due to the transfer learning.

After fine-tuning the second network, it will predict the diseases with a higher accuracy than any other previous method when given a never before seen medical image.

Stated differently, the target task permits the classifier to diagnose diseases of a medical patient based on a medical X-ray image for that medical patient, despite that particular medical X-ray image not being labeled whatsoever and despite that particular medical X-ray image having never been seen by the fine-tuned second CNN model at any time in the past.

With reference again to the data set forth at Table 1, the values in bold depict that of fourteen (14) total possible disease diagnoses, the above described process is capable of diagnosing 10 of the 14 total possible disease diagnoses with higher accuracy than any prior known methodology. The fine-tuned second CNN model will predict the diseases without human intervention and render a prediction accuracy (represented at the bottom data row of Table 1) with improved accuracy. The data shown here at Table 1 was generated via a "test phase" in which medical images from the ChestX-ray 14 data set was provided as input into the trained CNN model, but without any labels whatsoever, so as to provide a representative test and experiment of identifying and diagnosing diseases within the chest X-rays without the benefit of labeling of the various anatomical elements within the chest X-rays. Real-word application of the methodology as applied to medical patient chest X-rays is thus expected to be very consistent with the provided results.

According to particular embodiments, the self-supervised learning methodology leverages available chest X-rays from the ChestX-ray 14 data set to provide some supervision signals for training the proxy task utilized by the first CNN model described above (e.g., element 330 at FIG. 3 depicting the CVW classifier). The processing as set forth by the first step of the 3-step process as represented by FIG. 3 thus generates artificial labels as part of the "proxy task," and those artificial labels are then utilized by the self-supervised learning process.

According to certain embodiments, the intuition for the self-supervised learning process is derived from the chest X-ray depicted at FIG. 1A which has been annotated manually by a medical expert, for instance, showing the Carina, RA, LV, and Trachea anatomical elements, among others. These anatomical elements are recurring throughout all human patient medical chest X-rays, and thus, form a recurring pattern which may be exploited. Therefore, processing extracts the recurring pattern across all X-ray images in an automated manner, thus extracting a single patch containing the RA across all X-ray images and extracting the LV across all X-ray images, etc., thus performing an unsupervised machine learning process.

The extracted patches corresponding to, for example, RA is then defined as a "visual word," and similarly for LV, Carina, etc., there is a visual word defined for each anatomical element corresponding to the extracted image patches across the population of available X-ray images.

With prior techniques, it is not possible to transfer extracted visual words and therefore, it is necessary to rely upon curated and pre-labeled datasets. However, through practice of the described techniques, it is possible to transfer weights representing the defined visual words for the image patches extracted from the X-ray images from one CNN model capable of performing the diagnoses with greater accuracy over prior known methodologies. Stated differently, the weights representing the defined visual words for the image patches extracted from the X-ray images are now transferable from the "proxy task" CNN model to the "target task" CNN model. With the "target task" CNN model having received those transferred weights and having fine-tuned the second CNN model, it is then possible predict disease within never before seen medical X-ray images so as to diagnose diseases of medical patients.

Experiment settings: With respect to the Dataset. the effectiveness of TransVW methodology was evaluated for the multi-label chest X-ray classification target task utilizing the ChestX-Ray14 dataset (a publicly available hospital-scale chest X-ray dataset) which contains frontal-view chest X-rays of size 1024×1024 taken from 805 patients, where 708 images have at least one of the 14 chest pathologies. All of the experiments were conducted on the official patient-wise split of the dataset released.

With respect to the evaluation metric, performance of the described method was measured by reporting the Area Under the Curve (AUC) of each pathology as well as the mean AUC over all of the 14 pathologies.

Implementation: With respect to pretext tasks, in the CVW operation, random coordinates were selected to extract 224×224 patches. To perform image registration, KAZE was used for feature detection and matching; and cosine distance was used to calculate the similarity between the extracted descriptors. In the AVW operation, a sliding window of size 224×224 was used to find the instances of visual words within images. For the CVW and AVW classifiers, a DenseNet121 backbone was trained with input size of 224×224 using categorical cross-entropy loss. A U-Net architecture with DenseNet121 encoder and input size 224×224 was used in the ADS network. Additionally, two convolution and two fully connected layers were added at the end of the U-Net encoder, entitled "classifier block" (see FIG. 5), to perform the visual word classification. A Stochastic Gradient Descent optimizer (SGD optimizer) with learning rate 0.001 and decay 1e-6 was utilized for training the CVW, AVW, and ADS networks. Furthermore, for the sake of the evaluation, parameters $\alpha=0.01$, $\beta=0.99$, $N=200$, and $K=1000$ were set. Additionally, $M=100$ was set as the number of the visual word classes, through extensive experiments. The power of pre-trained models on ImageNet partially contributed to a large number of classes, in which 100 classes are maxed out in covering the chest field.

With regard to the target task, the encoder of the ADS network was utilized to initialize a DenseNet121 network for the target classification task, multi-label chest X-ray image classification. Each image was labeled with a one-hot vector $L=[L_0, L_1, \ldots, L_{14}]$. $L_0$ related to No finding and $L_1$ to $L_{14}$ related to each pathology. Every element $L_i$ represents the presence of the ith pathology, i.e., 1 for presence and 0 for absence. For multi-label classification, an ensemble of binary classifiers was considered, one for each pathology by using 15 binary cross-entropy loss functions. Images were resized to 448×448. For training, data augmentation techniques were performed including random rotation between 7 and horizontal flipping. In addition, crops were extracted from images with the sizes between 75% and 100% of the image area and the aspect ratio in range 3:4 and 4:3. An Adam optimizer was utilized with learning rate 0.0001. The same target model was trained three times and performed majority voting to calculate the final predictions. Early stopping was applied to stop training if validation loss did not improve for 10 epochs.

Results: With regard to baselines, when ChestX-ray14 was made available, only images were released without any official dataset splitting. Several works therefore utilized their own random split of this dataset to evaluate their respective methods. However, in the ChestX-ray14 dataset, there is an average of 3.6 images per patient. It is therefore possible that, through the random splitting, images of the same patient appear in both train and test sets simultaneously. Moreover, different random splits contribute to substantial variability in the performance. However, due to the randomness of splitting, reproducing the splits of dataset used by other studies is not feasible, which makes it hard to establish consistent benchmarks. An official patient-wise split of the ChestX-ray14 dataset was subsequently released, however, some of the prior implementations considered the official split of the dataset to have not been peer reviewed. So as to ensure a fair comparison, results of this evaluation were compared with all of the proposed methods that have considered official split of the dataset and are peer reviewed.

Transferable visual words methodology: Medical imaging protocols typically focus on particular parts of the body for specific clinical purposes, resulting in images of similar anatomy, such as the lungs in the case of chest X-rays (FIG. 1A), exhibiting complex, consistent and recurring patterns across acquired images. The described methodology exploits these sophisticated and recurrent patterns to learn a generalizable and transferable image representation for thorax disease identification in chest X-rays.

According to such embodiments, a visual word is defined as a segment of consistent and recurrent anatomical patterns, and instances of a visual word are defined as image patches (samples) extracted across different images for the same visual word. Naturally, all instances of the same visual word exhibit great similarity and consistency in appearance. Furthermore, a unique identifier, a visual word ID, is assigned to each visual word and consequently, all instances of a visual word share the same visual word ID.

The original bag-of-visual-word (BoVW) model first extracts the feature descriptors from images, and then clusters them to construct a visual dictionary. A significant drawback of conventionally known BoVW models is that the extracted visual words cannot be fine-tuned as is possible with a learned deep model. In addition, the extracted visual words may not be intuitive and explainable from the medical perspective, as they are automatically determined via unsupervised clustering algorithms rather than by an expert manually providing such annotations. So as to address these issues, the method TransVW methodology described herein automatically extracts visual words directly from images without clustering and integrates the BoVW unsupervised visual word extraction naturally with the CNN transferable representation learning power. More specifically, for chest X-ray image analysis, the TransVW methodology performs three discrete operations, including: (1) Coordinate-based Visual Word (CVW) Learning, (2) Anatomy-aware Visual Word (AVW) Learning, and (3) Anatomy-aware Dual-task Self-supervised (ADS) Learning.

With respect to (1) Coordinate-based Visual Word (CVW) Learning, as is illustrated in FIG. 3, a set of visual words is extracted based on fixed coordinates within chest X-ray images which are then utilized to train a classifier, called CVW classifier, with these extracted visual word instances and their IDs as ground truth. With regard to (2) Anatomy-aware Visual Word (AVW) Learning, as is illustrated in FIG. 4, the consistencies among extracted visual word instances are enhanced with the trained CVW classifier. Finally, with regard to the (3) Anatomy-aware Dual-task Self-supervised (ADS) Learning, as is illustrated in FIG. 5, visual word classification is incorporated with visual word restoration to further enhance the representation learning capability of TransVW.

These tasks and their goals are summarized in Table 2 at FIG. 9B. As shown by Table 2, the official training data of ChestX-ray14 is divided into two parts, specifically Part 1 and Part 2. The training images without disease labels in Part 1 are used for training the CVW classifier, while the training images without disease labels in Part 2 are used for training the AVW classifier as well as the ADS network. For the target task, the ADS encoder is fine-tuned with all the official training data with their disease labels. The 'w' and 'w/o' refer to with and without, respectively.

Coordinate-based visual word learning: As discussed above with respect to FIG. 2, notwithstanding the anatomies depicted across of medical images, several factors, such as the position of the patient's body, and the angle at which the image is taken, will have an influence upon the visual word extraction process. In fact, the instances of the same visual word can be located at different coordinates in different images. The challenge therefore is how to extract consistent instances of visual words across all images. A naive approach may select a specific coordinate in different images and then extracting instances of the visual word around that specific coordinate in all images. However, due to the aforementioned factors leading to the different coordinates of the instances of the same visual word in different images, such an approach yields an extensive variation among the anatomical patterns covered by visual word instances (see FIG. 2).

So as to extract consistent instances of visual words, as shown in FIG. 3, for each visual word, a random image is chosen from training data as a reference image; then, by using image registration technique, processing searches for and finds the N most similar images to that reference image. Then, a unique coordinate is chosen randomly, and processing extracts patches around it across all found images. This approach helps that instances of a visual word, which are extracted at the same coordinate in similar images, cover the similar anatomical part (FIG. 2). After extracting the instances of all M visual words, a CNN is then trained to classify these instances into M classes with their visual word IDs as ground truth. Details of the CVW procedure is shown by Algorithm 1 as set forth at FIG. 9A.

Anatomy-aware visual word learning: Due to limitations of existing feature detectors and matching algorithms for image registration in the medical domain, some of the found images in the coordinate-based visual word extraction procedure may not be similar to the reference image. Consequently, if instances of a visual word from a specific coordinate across all found images are extracted, there may be some inconsistent instances within each class of visual words. Therefore, processing via the described embodiments operate to increase the consistency of instances of visual words by utilizing the pre-trained CVW classifier (see FIG. 4). The sliding window is specifically utilized on the unseen training data (Part 2) to extract patches and then pass them to the CVW classifier to find the M visual words of each image. Then, among all of the found instances of a visual word across all images, the K most confident instances are selected based on the output probability of the CVW classifier. Unlike the CVW step, during which instances of a visual word are extracted from a specific coordinate, during the AVW step the instances of the same visual word may have different coordinates in different images. Processing therefore ensures that the different instances of the same visual word cover the same part of the anatomical structure. Further still, so as to produce more robust anatomical features, the AVW classifier is trained to classify these new and more consistent visual words into M classes. Refer to Algorithm 2 as set forth at FIG. 9B, which provides further details of AVW procedure.

FIG. 6 depicts an exemplary visual comparison of localizing ten different visual word instances by CVW classifier (top row 601), AVW classifier (bottom row 604) in the same test images, as well as zoomed in views of CVW localization (second row 602) and AVW localization (third row 603), in accordance with described embodiments.

Evidently, there are inconsistencies in appearance among the visual word instances extracted by the CVW classifier (arrows in top row 601), with corresponding zoomed views in second row 602. In contrast, a high degree of appearance consistency is exhibited among the instances localized using the AVW classifier for the same visual word (third row 603). More consistent instances of a visual word are localized by using AVW classifier than CVW classifier since AVW classifier is trained with more consistent instances of visual words than CVW classifier. AVW learns more robust representation and hence performs better than the CVW classifier on target tasks.

Figure 7A:
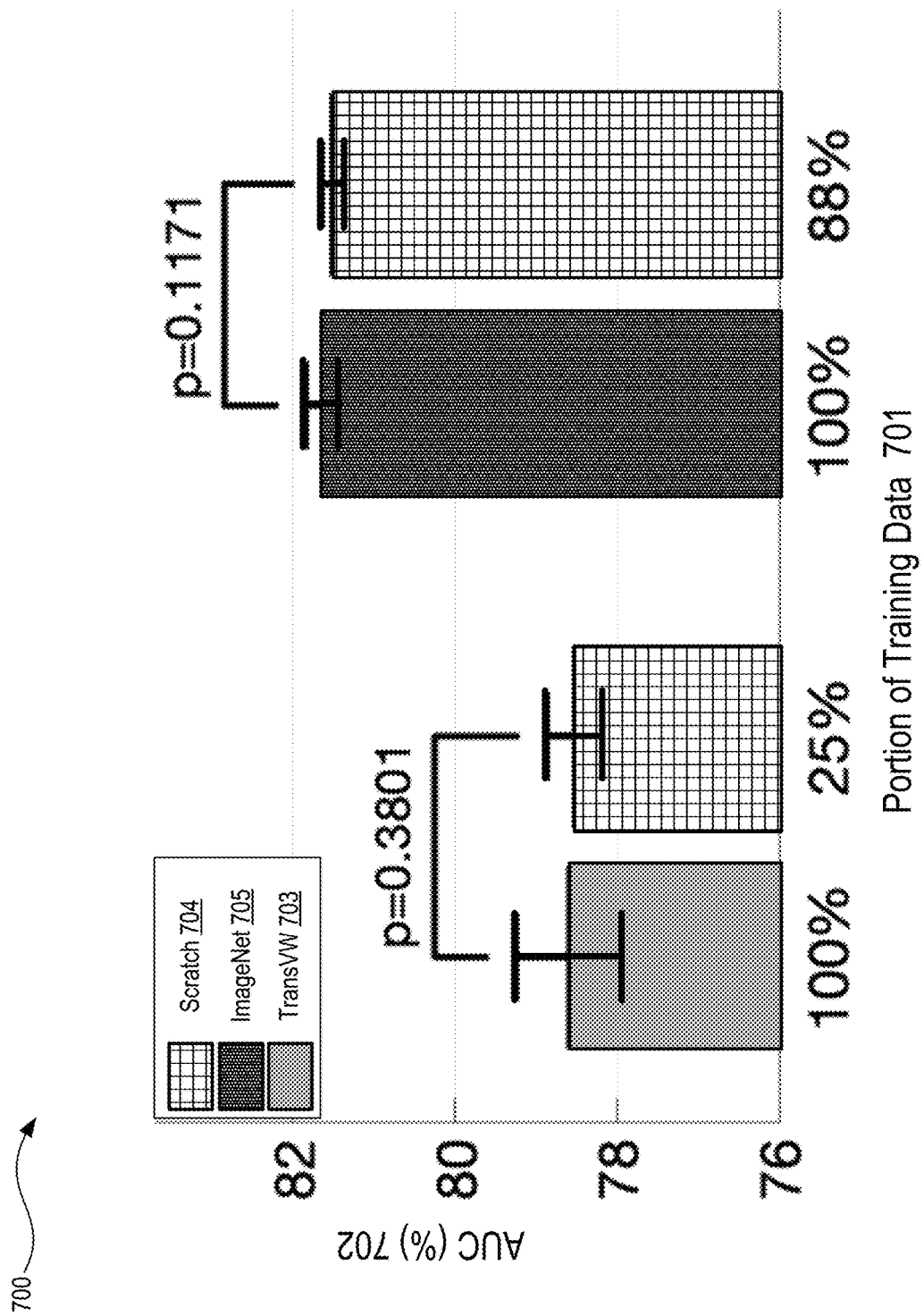
FIG. 7A depicts a graphical comparison of annotation effort AUC (%) for TransVW compared to training from scratch and fine-tuning a pre-trained ImageNet model, based on the portion of training data available, in accordance with described embodiments.

FIG. 7A depicts a graphical comparison 700 of annotation effort AUC (%) 702 for TransVW 703 compared to training from scratch 704 and fine-tuning a pre-trained ImageNet model 705, based on the portion of training data available 701, in accordance with described embodiments.

As shown here, initializing the target model with TransVW reduces the annotation efforts by 75% and 12% relative to training a model from scratch and fine-tuning a pre-trained ImageNet model, respectively.

By utilizing only 25% of the labeled data in the target pass it is possible to attain the same accuracy as training from scratch utilizing 100% of the labeled data, thus providing a 75% annotation cost savings and making for a much more efficient process, thus saving time and computational resources. It therefore is unnecessary to rely upon human intervention to label the additional 75% of data as similar results are attainable with only the 25% portion of the labeled training data.

On the right hand side of the diagram it is depicted that a large ImageNet data set (element 705) with approximately 14 million images is utilized by prior known techniques which requires extensive computational resources. Using the 88% of the training data of our target task dataset (ChestX-ray14), our method achieves same performance on target task as the ImageNet pre-trained model which use 100% of training data of ChestX-ray14 dataset, thus providing for greater efficiency through time savings and reduced human annotation efforts.

With 25% training data, TransVW achieves performance equivalent to training from scratch with 100% training data (p-value>0.05). With 88% training data, TransVW offers performance equivalent to fine-tuning a pre-trained ImageNet model with 100% training data (p-value>0.05), thereby reducing annotation efforts by 75% relative to training from scratch and by 12% relative to fine-tuning a pre-trained ImageNet model.

Ablation study experiments using ResNet18 architecture for improved speed were performed, each run at least ten times on the target task. To make a fair comparison, different hyper parameters are examined and the best result of each method is reported. For more accurate comparison, the average AUC over the 14 chest pathologies, standard deviation, and statistical analysis based on independent two-sample t-test are reported for all experiments.

First, to emphasize the significance of specifically designed self-supervised tasks for medical images, the ablation studies demonstrate that AVW outperforms other self-supervised approaches, which are proposed for natural images instead of medical images. Second, the contribution of AVW's contributions to the ADS are demonstrated by providing the performance of the isolated AVW classification and visual word reconstruction tasks on the target task. Also, the combination of the AVW with different image restoration tasks improves the performance of those image restoration tasks. AVW also has target performance superiority over CVW.

Figure 7B:
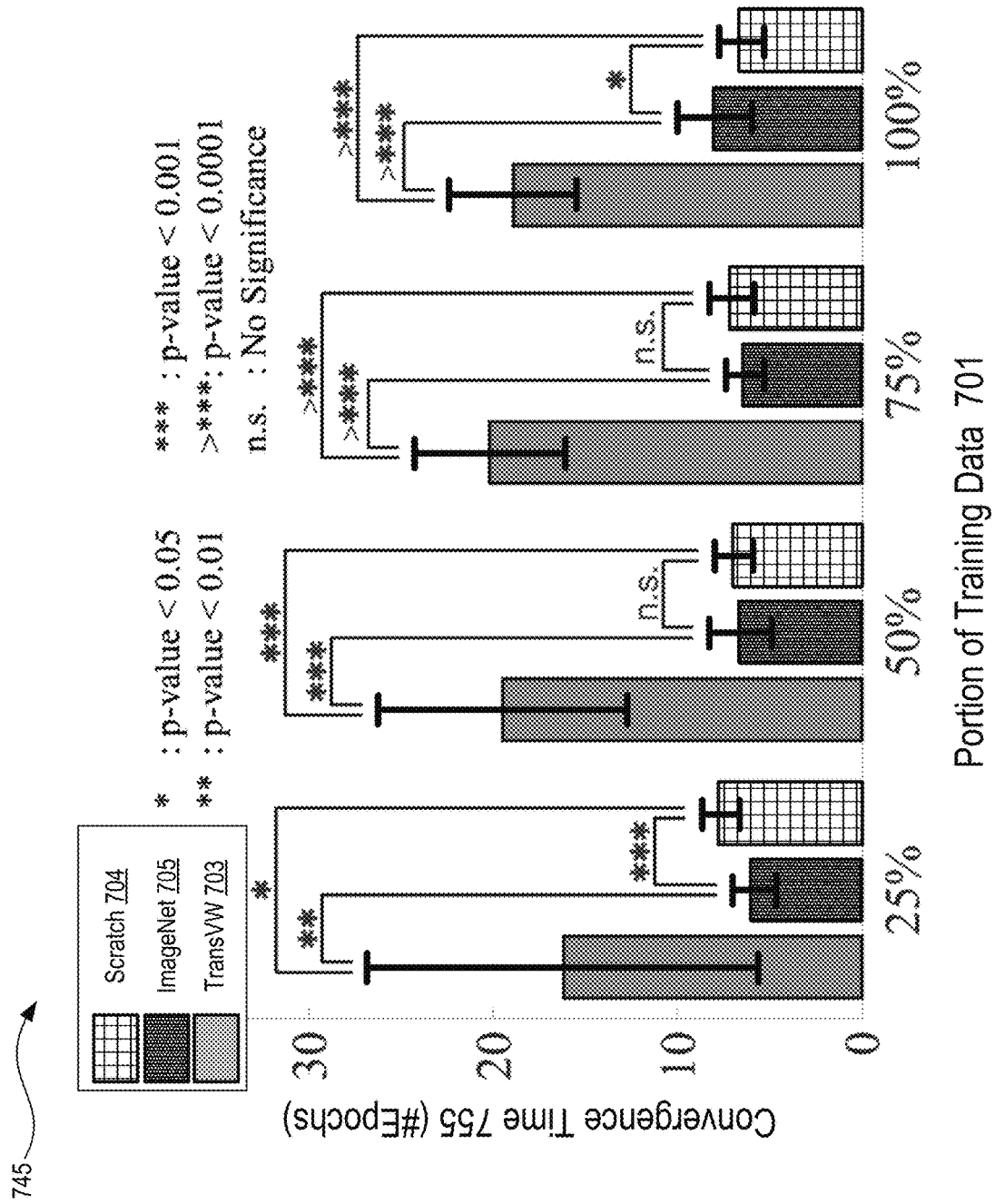
FIG. 7B illustrates a chart showing that with 100% of the dataset, fine-tuning from the TransVW method converges significantly faster than that from ImageNet, according to described embodiments.

FIG. 7B illustrates a chart 745 showing that with 100% of the dataset, fine-tuning from the TransVW method converges significantly faster than that from ImageNet, while offering an equivalent convergence speed with 50% or 75% of the dataset as depicted by the convergence time 755 on the vertical axis. It becomes slower with 25% dataset, which is not critical for this application given the performance, as depicted by the portion of training data 701 depicted via the horizontal axis.

TransVW outperforms state-of-the-art multi-label chest X-ray image classification: The results in Table 1 demonstrate that fine-tuning from the proposed TransVW model yields superior performance over all existing SOTA ChestX-ray14 classification methods. In addition to achieving the best average over fourteen pathologies, TransVW achieves the best performance on ten pathologies. The TransVW is the first known method and implementation which successfully utilizes self-supervised approach for X-Ray modality to achieve the best performance in multi-label chest X-ray image classification whereas previously known methods operate by fine-tuning the pre-trained ImageNet models.

TransVW outperforms the models trained from scratch or pre-trained with ImageNet: So as to fairly and accurately compare the TransVW method as described herein with previously known supervised pre-training techniques, i.e. pre-training on ImageNet, comparisons are made for the classification performance, convergence time, and annotation saving of TransVW with training from scratch (lower bound) and pre-training on ImageNet (upper bound) on target task. The same models were trained and were initialized randomly, with ImageNet, and with TransVW on the target task. Results of statistical analysis based on independent two-sample t-test for 10 runs in Table 3 show that TransVW significantly outperforms models trained from scratch or pre-trained with ImageNet (p-value<0.05). Additionally, TransVW still has the best performance when the training data is reduced to 25%, 50%, 75%, and 88%. For comparison of methods pathology-by-pathology, please refer to the Appendix. Moreover, as illustrated in FIG. 6, TransVW reduces the annotation efforts on target task by 75% and 12% relative to training a model from scratch and fine-tuning a pre-trained ImageNet model, respectively. Additionally, as shown in FIG. 7B, using 100% of training data, TransVW converges faster than ImageNet on target task, and has equivalent convergence time when using 50% and 75% of data. TransVW is always significantly faster than training from scratch.

Table 3 shows that fine-tuning models from TransVW significantly outperform models of the same architecture trained from scratch or fine-tuned from ImageNet on the NIH ChestXray14 classification, even with reduced training size.

To fairly and accurately compare the TransVW with training from scratch and pre-training with ImageNet, the same vanilla models which initialized randomly are trained with ImageNet and TransVW on a target task. Results of statistical analysis based on independent two-sample t-test for 10 runs in Table 3 show that TransVW significantly outperforms models trained from scratch or pre-trained with ImageNet (p-value<0.05). Additionally, TransVW still has the best performance when the training data is reduced to 25%, 50%, 75%, and 88% ('Training Data' column in Table 3).

The results in Table 4A further demonstrate that pre-trained model on an AVW classification task significantly outperforms models of the same architecture trained from scratch as well as fine-tuned from other self-supervised approaches (p-value<0:05).

Moreover, existing self-supervised approaches have equivalent performance to training from scratch in medical domain (p-value>0:05), which shows that the self-supervised pretexts which perform well in natural images may not be effective in the medical domain. In fact, the dense anatomical patterns (visual words) in X-rays seem to make them learn trivial solutions, leading to poor performance, an observation that inspired development of the concept of transferable visual words. Also, superior performance of a self-supervised task shows that utilization of the unique attributes of the medical images in designing the self-supervised pretexts yields more relevant representation in the medical images domain.

The results in Table 4B demonstrate that fine-tuning from TransVW significantly outperforms fine-tuning from other self-supervised approaches on the ChestX-ray14 multi-label pathology classification task.

To demonstrate the contribution of the AVW in the performance of ADS, performance results of the single elastic transformed image restoration task on the target task is provided at Table 5. The combination of the AVW with elastic transformed image restoration task elevate the performance of elastic transformation and also AVW by itself.

Moreover, two other image reconstruction tasks, in-painting and auto-encoder, are combined with AVW in the disclosed ADS network. Based on Table 5, combining AVW with auto-encoder and in-painting improves the performance of those individual tasks as well.

TransVW outperforms other self-supervised methods: The results in Tables 4A and 4B therefore demonstrate that a pre-trained model on TransVW significantly outperforms models of the same architecture that fine-tuned from other self-supervised approaches. Moreover, other self-supervised approaches have equivalent performance to training from scratch in the medical domain, which shows that the self-supervised pretexts which perform well in natural images may not be effective in the medical domain. Also, the encoder of ADS network (TransVW) significantly outperforms the AVW classifier on target task, demonstrating the effect of dual-tasks in representation learning.

In such a way, the transferable visual words (TransVW) methodology, provides a self-supervised approach utilizing the recurrent anatomical structure in medical images to learn common and transferable image representation. As shown herein, TransVW outperforms SOTA methods in ChestX-ray14 thorax classification task. In addition, TransVW outperforms training from scratch and pre-training with ImageNet in both classification performance and convergence time, which leads to reducing annotation costs in chest X-ray image analysis.

Figure 7C:
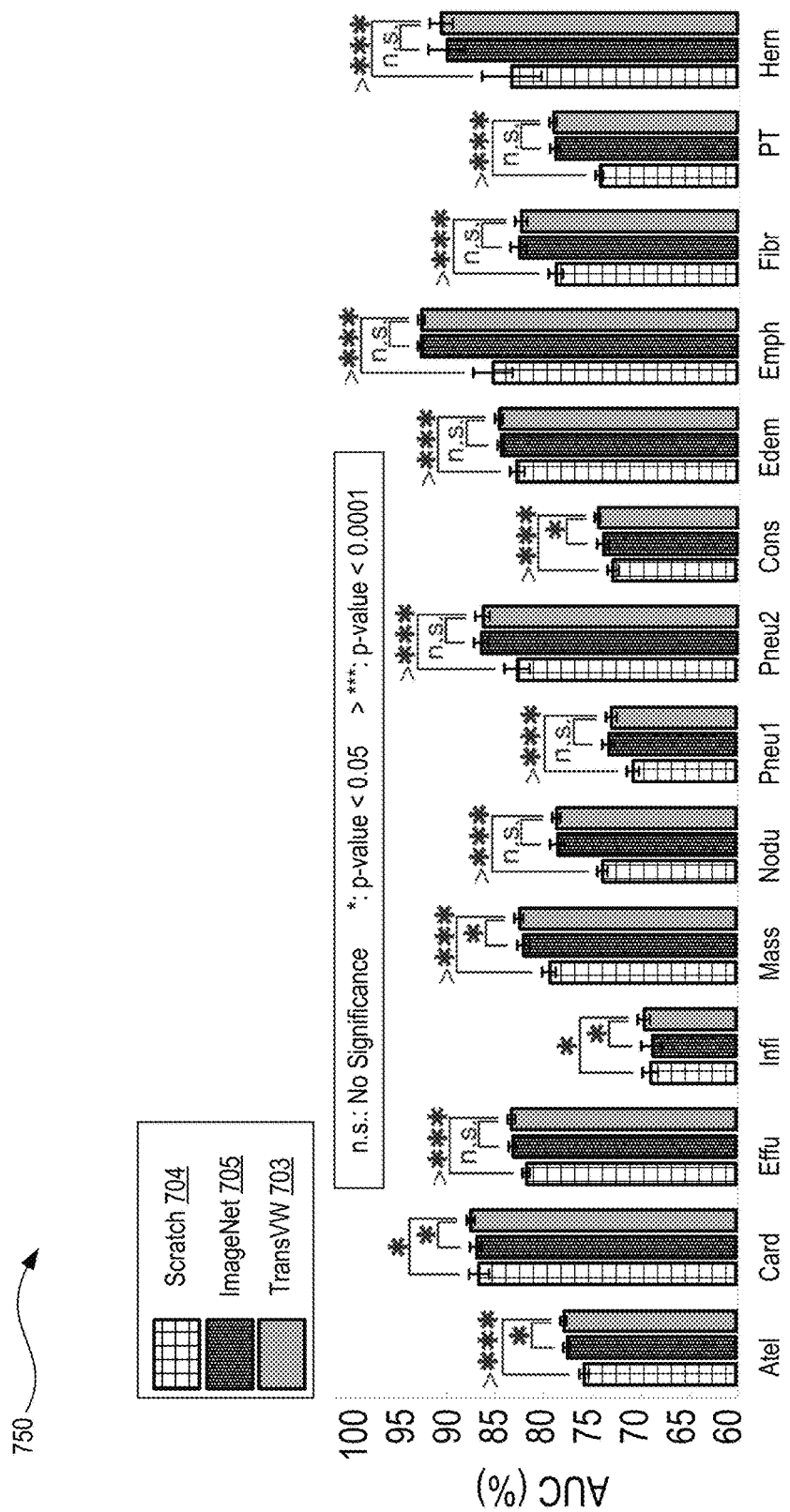
FIG. 7C illustrates a chart showing that TransVW significantly outperforms training from scratch in all 14 pathologies.

FIG. 7C illustrates a chart 750 showing that TransVW significantly outperforms training from scratch in all 14 pathologies. Moreover, TransVW significantly outperforms ImageNet in five (5) pathologies, specifically Atel, Cadr, Infi, Mass, and Cons, and has equivalent performance with ImageNet in the remaining pathologies.

Notably, the described methodology is considered more annotation efficient than prior known methods when the disclosed methodology: (1) achieves better performance than prior known methods when using the same amount of annotated training data, (2) reduces the training time in comparison with prior known methods using the same amount of annotated data, or (3) offers the same performance as prior known methods but requires less annotated training data.

Naturally, in comparison with training from scratch or fine-tuning from pre-trained ImageNet models, the disclosed TransVW methodology is annotation efficient since it achieves better performance as depicted by Table 6A at FIG. 9G, reduces training time Table 6B at FIG. 9G, and reduces the amount of annotated data Table 6C at FIG. 9G. Furthermore, in multi-label thorax disease classification task, correctly diagnosing each and every disease is clinically critical; therefore, the mean AUC metric may not be sufficient when comparing the methods on this dataset. As a result, statistical tests are reported on a pathology-by-pathology basis via chart 750, demonstrating the performance gain from TransVW. In all experiments, we train models of the same architecture were trained, and statistical analysis results were reported, based on the independent two-sample t-test from 10 runs. All the p-values are calculated between TransVW and competing prior known methods, in which p-value<0.05 indicates the superiority of TransVW over competitor methods in Table 6A, Table 6B, and chart 750 at FIG. 7C, while p-value>0.05 (e.g., "n.s.") indicates the equality in performance of TransVW with other methods in Table 6C and chart 750 at FIG. 7C.

Figure 7D:
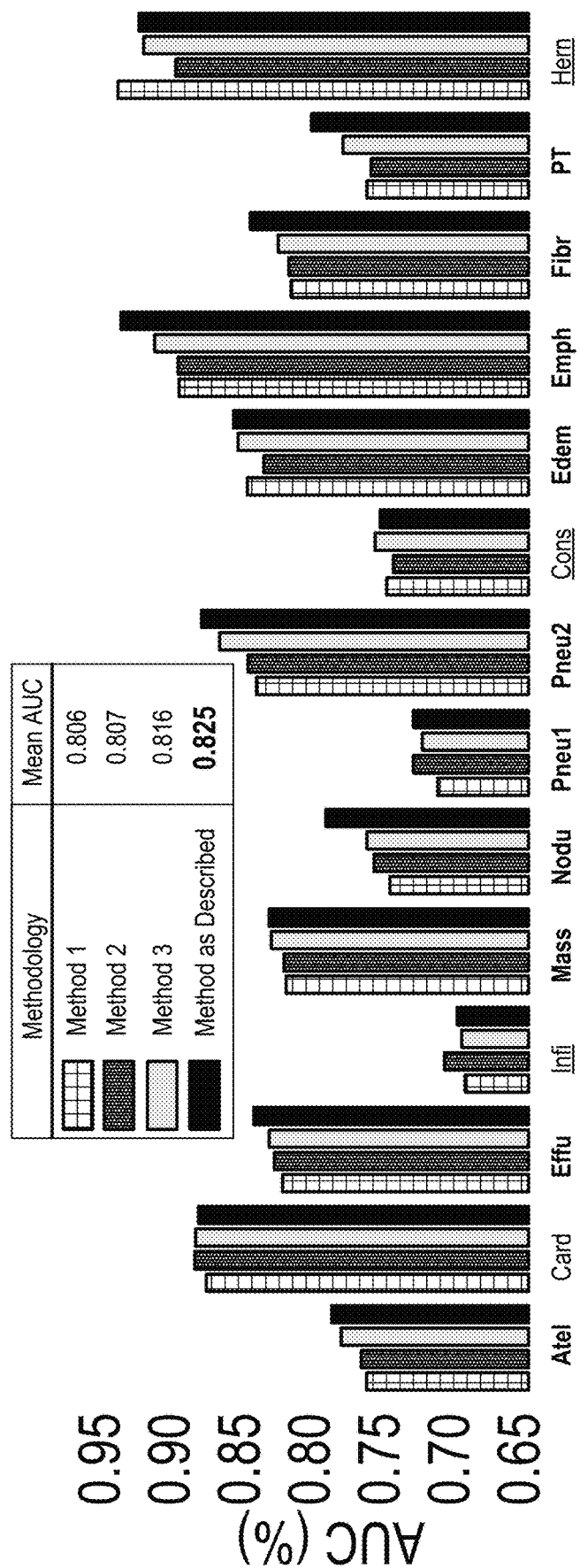
FIG. 7D illustrates a chart showing that TransVW outperforms state-of-the-art (SOTA) methods in multi-label chest X-ray image classification.

FIG. 7D illustrates a chart 755 showing that TransVW outperforms state-of-the_art (SOTA) methods in multi-label chest X-ray image classification.

More particularly, TransVW was compared with the three best prior known methods, which have the highest mean AUC. Fine-tuning the model from TransVW achieves the best average AUC over all 14 diseases among all prior known methods. Moreover, the method as described herein achieves the best AUC performance in 10 out of 14 individual pathologies (in bold) and the described methodology has the second best AUC performance in three (3) pathologies (underlined).

Algorithms 1 and 2: details of the extraction of coordinate-based visual word (CVW) and Anatomy-aware Visual Word (AVW) are provided via Algorithms 1 and 2 as set forth in FIG. 8A and FIG. 8B, respectively.

FIG. 8A depicts an algorithm for CVW extraction in accordance with described embodiments.

FIG. 8B depicts an algorithm for AVW extraction in accordance with described embodiments.

Although the coordinate-based visual word (CVW) extraction method yields similar anatomical pattern within instances of a visual word, there are some instances which are not completely similar to the rest. Hence, the anatomy-aware visual word extraction step provides more consistent instances of visual words for training the AVW classifier. In fact, the CVW classifier is used to select the most confident instances of each visual word among images. Hence, the AVW classifier is trained on visual word instances with a great degree of consistency. As a result, the AVW classifier learns more robust visual word representation than the CVW classifier, which extracts more consistent instances of visual words among images.

As previously described, a visual word corresponds to a segment of a consistent and recurrent anatomical pattern. For example, instances of a visual word may be image patches (samples) extracted across different images for the same visual word.

FIG. 9A sets forth Table 1, which lists the mean performances of TransVW compared to SOTA across 14 pulmonary pathologies from the ChestX-ray14 Dataset.

FIG. 9B sets forth Table 2, which lists the division of Chest-Xray14 training data for training of classifiers and ADS encoder for performance of tasks to achieve the goals of TransVW.

FIG. 9C sets forth Table 3, which details how TransVW outperforms the models trained from scratch or pre-trained with ImageNet.

FIG. 9D sets forth Table 4A, which details how AVW outperforms the models trained from scratch or fine-tuned from other self-supervised methods.

FIG. 9E sets forth Table 4B, which demonstrates that fine-tuning from TransVW significantly outperforms fine-tuning from other self-supervised approaches on the ChestX-ray14 multi-label pathology classification task.

FIG. 9F sets forth Table 5 which details the contribution of AVW in the performance of ADS, in accordance with described embodiments.

FIG. 9G sets forth Tables 6A, 6B, and 6C, which detail the performance (a), training time (b), and the annotation savings (c) provided through the use of the TransVW methodology over ImageNet or by training from scratch, in accordance with described embodiments.

FIGS. 10A, 10B, 10C and 10D provide a depiction of 70 instances of four visual words extracted from Part 2 of ChestX-ray14 training images using the CVW classifier, in accordance with described embodiments.

The most confident instances of the four visual words shown in FIG. 10A-10D were obtained using the CVW classifier through the steps of AVW learning shown in FIG. 4. Each visual word covers a specific anatomical pattern which is repeated in almost all instances of the visual word. The appearance consistency of the visual words instances is the product of TransVW's two-step visual word extraction method involving CVW and AVW. These visual word instances are used to train the AVW classifier and ADS network.

Figure 10A:
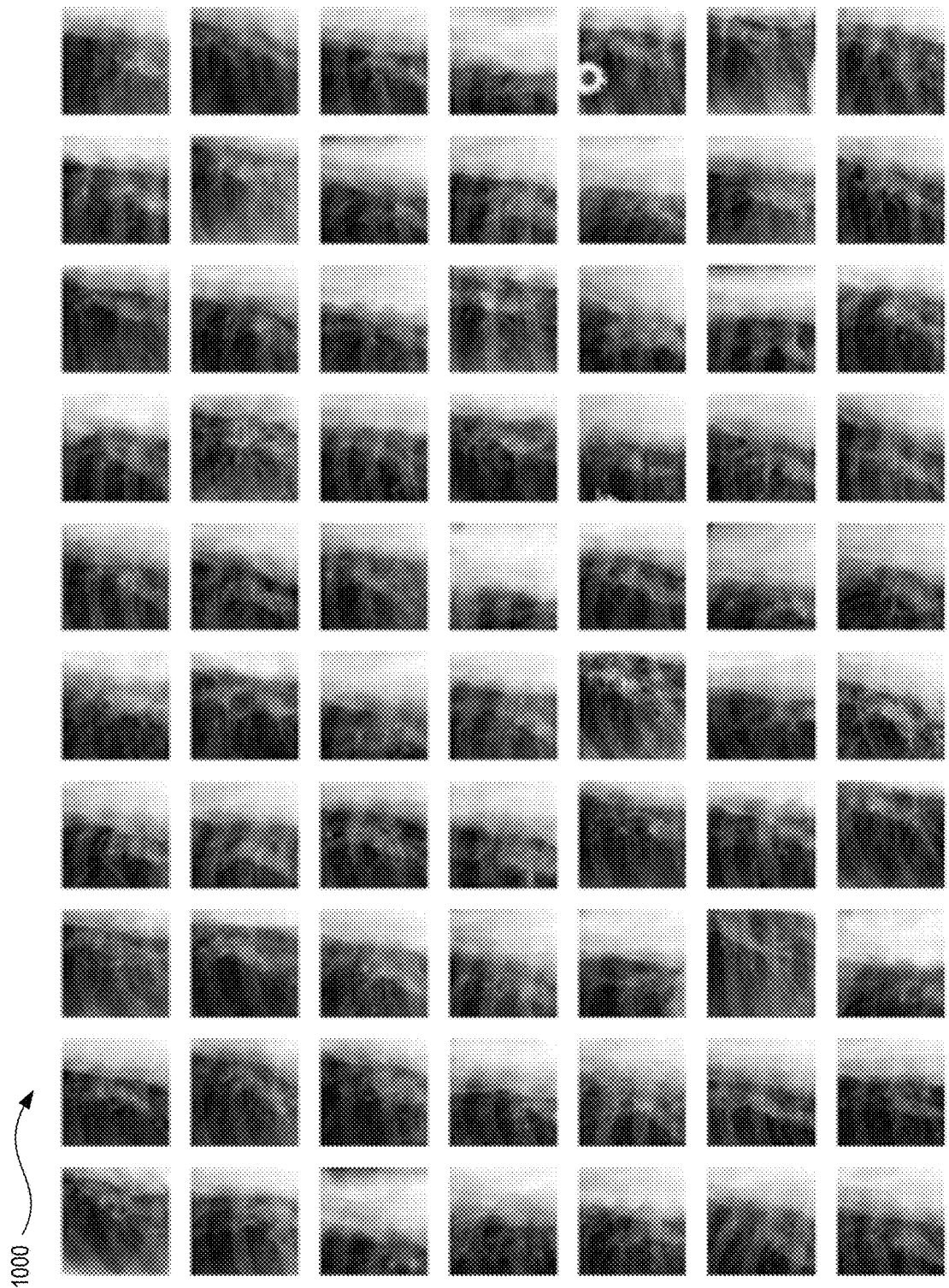
FIGS. 10A, 10B, 10C and 10D provide a depiction of 70 instances of four visual words extracted from Part 2 of ChestX-ray14 training images using the CVW classifier, in accordance with described embodiments.

FIG. 10A is a depiction of the most confidence instances of the visual word "right pulmonary artery" obtained using a two-step visual word extraction method using a CVW classifier through the steps of AVW, in accordance with described embodiments.

Figure 10B:
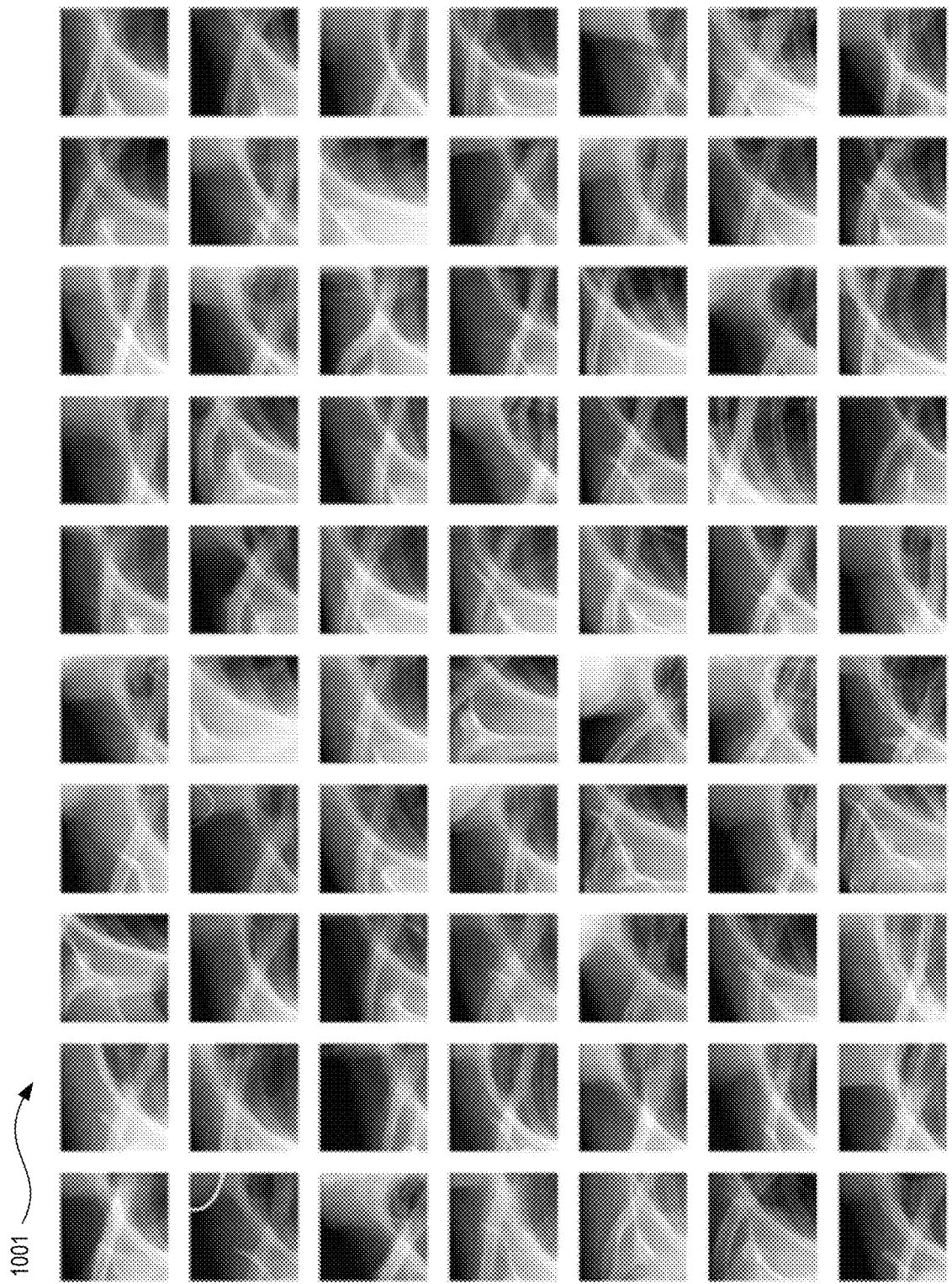

FIG. 10B is a depiction of the most confidence instances of the visual word "right clavicle" obtained using a two-step visual word extraction method using a CVW classifier through the steps of AVW, in accordance with described embodiments.

Figure 10C:
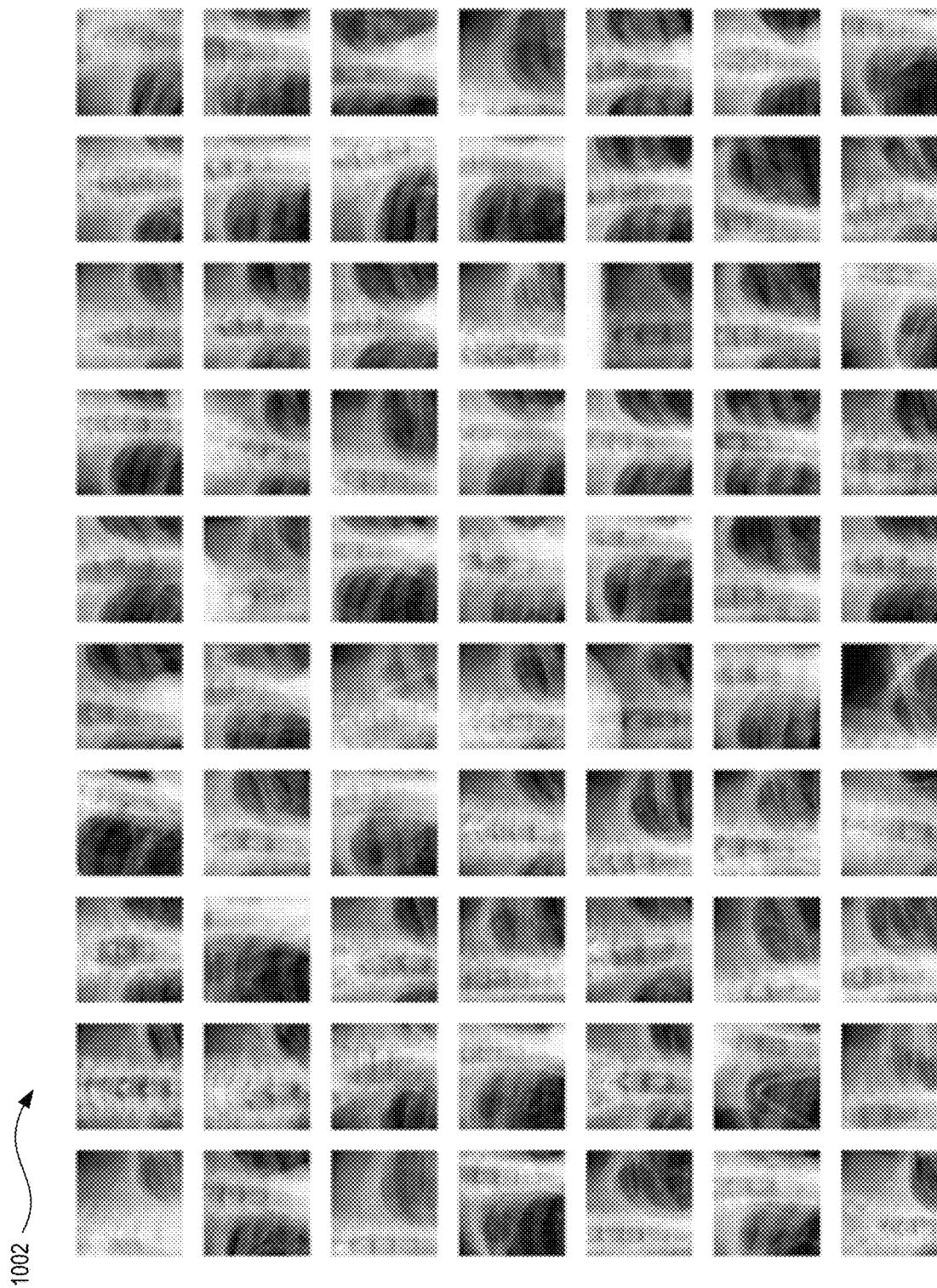

FIG. 10C is a depiction of the most confidence instances of the visual word "spinous processes" obtained using a two-step visual word extraction method using a CVW classifier through the steps of AVW, in accordance with described embodiments.

Figure 10D:
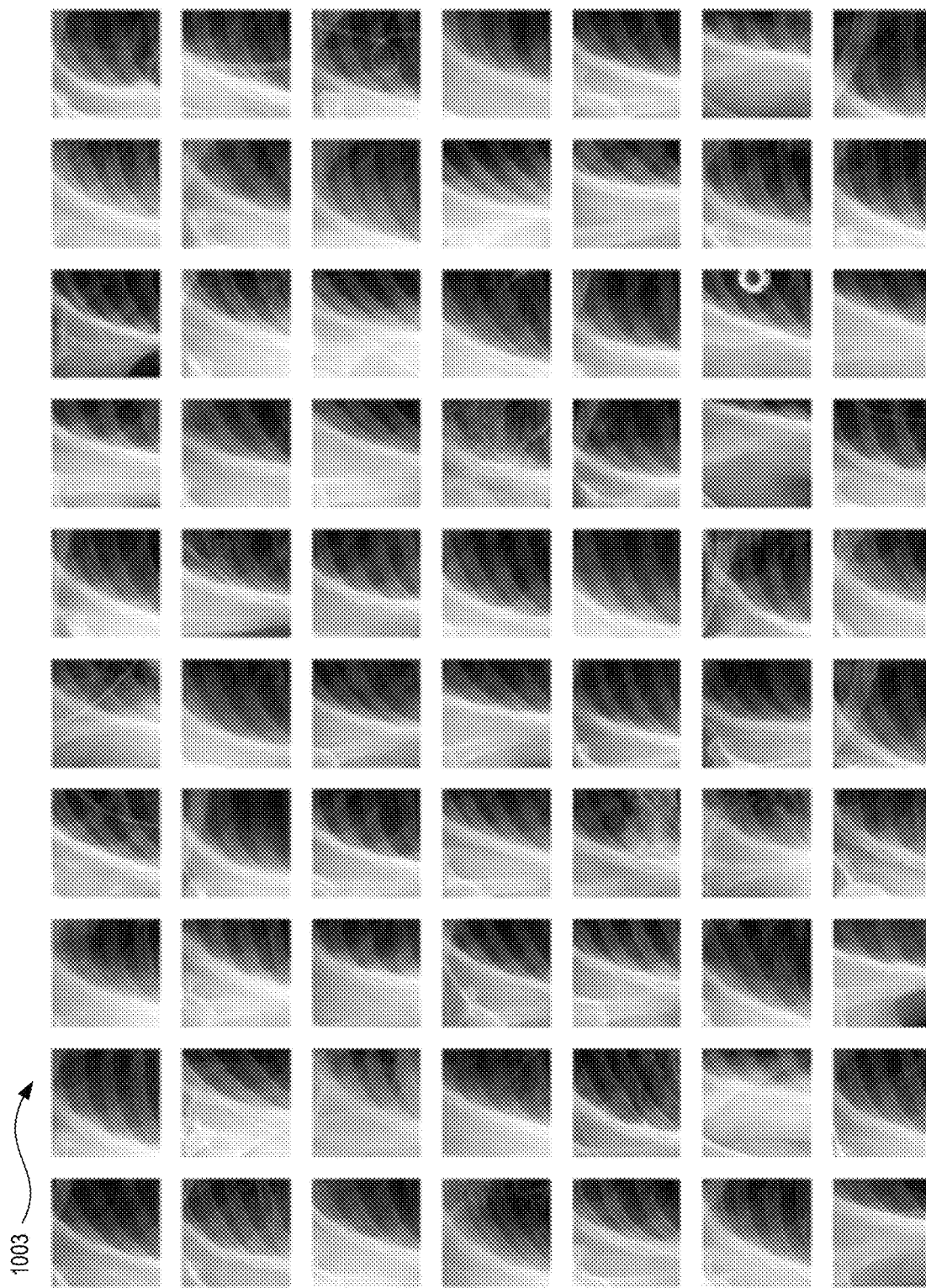

FIG. 10D is a depiction of the most confidence instances of the visual word "$3^{rd}$-$6^{th}$ posterior ribs" obtained using a two-step visual word extraction method using a CVW classifier through the steps of AVW, in accordance with described embodiments.

Each visual word covers a specific anatomical pattern which is repeated across all images. Referring back to the expert annotation in FIG. 1A, these four visual words cover the (a) right pulmonary artery, (b) right clavicle, (c) Spinous processes, and (d) 3rd-6th posterior ribs, respectively. These recurrent patterns may be self-supervision signals.

The consistency among the instances of visual words comes from the two stages of visual word extraction as described herein, specifically the coordinate-based visual word (CVW) extraction followed by anatomy-aware visual word (AVW) extraction. These consistent visual word instances are used to train the AVW classifier as well as the ADS network to learn generalizable and transferable image representation.

Figure 11:
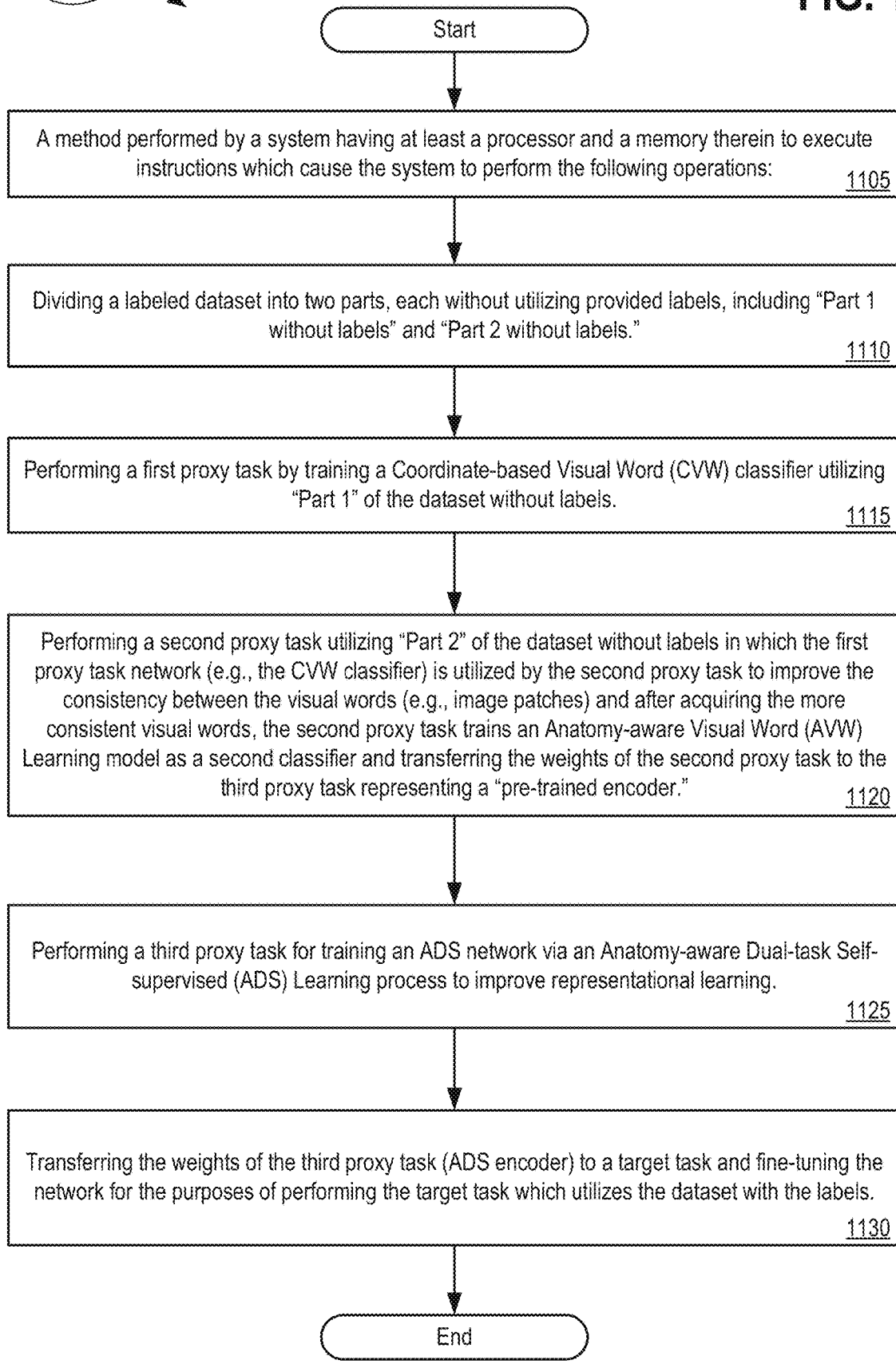
FIG. 11 depicts a flow diagram illustrating a method for implementing a self-supervised chest x-ray image analysis machine-learning model utilizing transferable visual words, in accordance with disclosed embodiments.

FIG. 11 depicts a flow diagram illustrating a method 1100 for implementing a self-supervised chest x-ray image analysis machine-learning model utilizing transferable visual words, in accordance with disclosed embodiments.

Method 1100 may be performed by processing logic that may include hardware (e.g., circuitry, dedicated logic, programmable logic, microcode, etc.), software (e.g., instructions run on a processing device) to perform various operations such as designing, defining, retrieving, parsing, persisting, exposing, loading, executing, operating, receiving, generating, storing, maintaining, creating, returning, presenting, interfacing, communicating, transmitting, querying, processing, providing, determining, triggering, displaying, updating, sending, etc., in pursuance of the systems and methods as described herein. For example, the system 1201 (see FIG. 12) and the machine 1301 (see FIG. 13) and the other supporting systems and components as described herein may implement the described methodologies. Some of the blocks and/or operations listed below are optional in accordance with certain embodiments. The numbering of the blocks presented is for the sake of clarity and is not intended to prescribe an order of operations in which the various blocks must occur.

With reference to the method 1100 depicted at FIG. 11A beginning at block 1105, there is a method performed by a system having at least a processor and a memory therein to execute instructions which cause the system to perform the following operations:

At block 1110, processing logic divides a labeled dataset into two parts, each without utilizing provided labels, including "Part 1 without labels" and "Part 2 without labels."

At block 1115, processing logic performs a first proxy task by training a Coordinate-based Visual Word (CVW) classifier utilizing "Part 1" of the dataset without labels.

At block 1120, processing logic performs a second proxy task utilizing "Part 2" of the dataset without labels in which the first proxy task network (e.g., the CVW classifier) is utilized by the second proxy task to improve the consistency between the visual words (e.g., image patches) and after acquiring the more consistent visual words, the processing logic performs the second proxy task by training an Anatomy-aware Visual Word (AVW) Learning model as a second classifier and transferring the weights of the second proxy task to the third proxy task representing a "pre-trained encoder."

At block 1125, processing logic performs a third proxy task for training an ADS network via an Anatomy-aware Dual-task Self-supervised (ADS) Learning process to improve representational learning.

At block 1130, processing logic transfers the weights of the third proxy task (ADS encoder) to a target task and fine-tuning the network for the purposes of performing the target task which utilizes the dataset with the labels.

According to another embodiment of method 1100, a target CNN model is fine-tuned to be capable of performing identification of X-ray image elements and diagnosis of diseases within such X-ray images for never before seen X-ray images which are not part of any training dataset.

According to another embodiment, method 1100, further includes: classifying disease in previously unseen medical images by performing identification of X-ray image elements and diagnosis of diseases within such X-ray images for never before seen X-ray images which are not part of any training dataset.

According to another embodiment of method 1100, the medical images are not manually annotated.

According to another embodiment of method 1100, the medical images are chest X-ray medical images.

According to another embodiment of method 1100, the learned model is transferred to a target application that classifies thorax disease, wherein the disease is present in chest X-rays.

According to another embodiment of method 1100, a first sub-operation implements coordinate-based visual word (CVW) learning, including: selecting, at random, a medical image to serve as a reference image for a visual word, wherein the visual word is assigned a visual word ID i; identifying, via an image registration technique, the top N-most similar images to the selected reference image from an image dataset, wherein N is the number of instances of each visual word; extracting patches at a randomly-generated unique coordinate across the top N-most similar images; repeating extraction for all visual words of interest; and training the CVW classifier to classify the visual words into M classes, wherein M is the number of visual word classes.

According to another embodiment of method 1100, the unique coordinate is randomly generated at an ith coordinate.

According to another embodiment of method 1100, the second sub-operation further comprises applying an Anatomy-aware visual word (AVW) learning model, including:

generating image patches, wherein the image patches are generated by sliding a window on each image in a given training set; inputting the generated patches to the CVW classifier to localize visual words in each image; selecting the top K-most confident instances of each visual word among all images, wherein K is the number for instances of each visual word; and training an AVW classifier to classify the visual words into M classes, wherein M is the number of visual word classes.

According to another embodiment of method 1100, in which the AVW classifier serves as an encoder for a self-supervised U-Net-like dual-task learner network, the network comprising a deformed visual word input, wherein the deformed visual word is generated by applying elastic transformation on a visual word, wherein elastic transformation involves spatial-level deformation of the visual word input; and further in which an Anatomy-aware Dual-task Self-supervised (ADS) learning process deforms each input visual word instance using elastic transformation.

According to a particular embodiment, there is a non-transitory computer readable storage media having instructions stored thereupon that, when executed by a system having at least a processor and a memory therein, the instructions cause the system to perform operations including: executing, via the processor, a Convolutional Neural Network (CNN) model stored within the memory of the system, wherein the CNN model is self-supervised for generalizable and transferable image representation of medical images; identifying visual words via the executing CNN model, wherein the visual words are consistent and recurring patterns involving anatomical structures across medical images; transferring learned weights from the CNN model representing identified visual words from an initial CNN model to another CNN model capable of performing the "target task" for diagnosis of disease by fine-tuning the transferred weights, wherein instances of the visual words correspond to sample patches of images extracted across multiple different images for the same visual word, and further wherein the extraction of the instances is performed in via two sub-operations, including: (i) a first sub-operation to execute via the processor of the system by extracting patches around a unique coordinate across all of the available medical images, and (ii) a second sub-operation to execute via the processor of the system by generating patches from an entire image to localize visual words; selecting the top-most confident instances and further reducing inconsistencies among extracted instances of a visual word from the first sub-operation; and classifying disease in previously unseen medical images using the weights of a third CNN, the Anatomy-aware Dual-task Self-supervised (ADS) Learning model, which are transferred to a target task, after the second CNN model performs the "target task" by fine-tuning the learned weights from the first CNN model.

As discussed above, part 1 of the dataset without disease labels is utilized by the first proxy task to train the Coordinate-based Visual Word (CVW) classifier while part 2 of the dataset without labels is utilized by the second proxy task in which the first proxy network (e.g., the CVW classifier) is utilized by the second proxy task to improve the consistency between the visual words (e.g., image patches). Once the more consistent visual words are obtained, the Anatomy-aware Visual Word (AVW) Learning model is trained as the second classifier and then the weight of the second proxy task is transferred to the third proxy task. Finally, the encoder's weights of the third proxy task are transferred to the target task and the network is fine-tuned for the purposes of the target task which utilizes the dataset with the labels.

Figure 12:
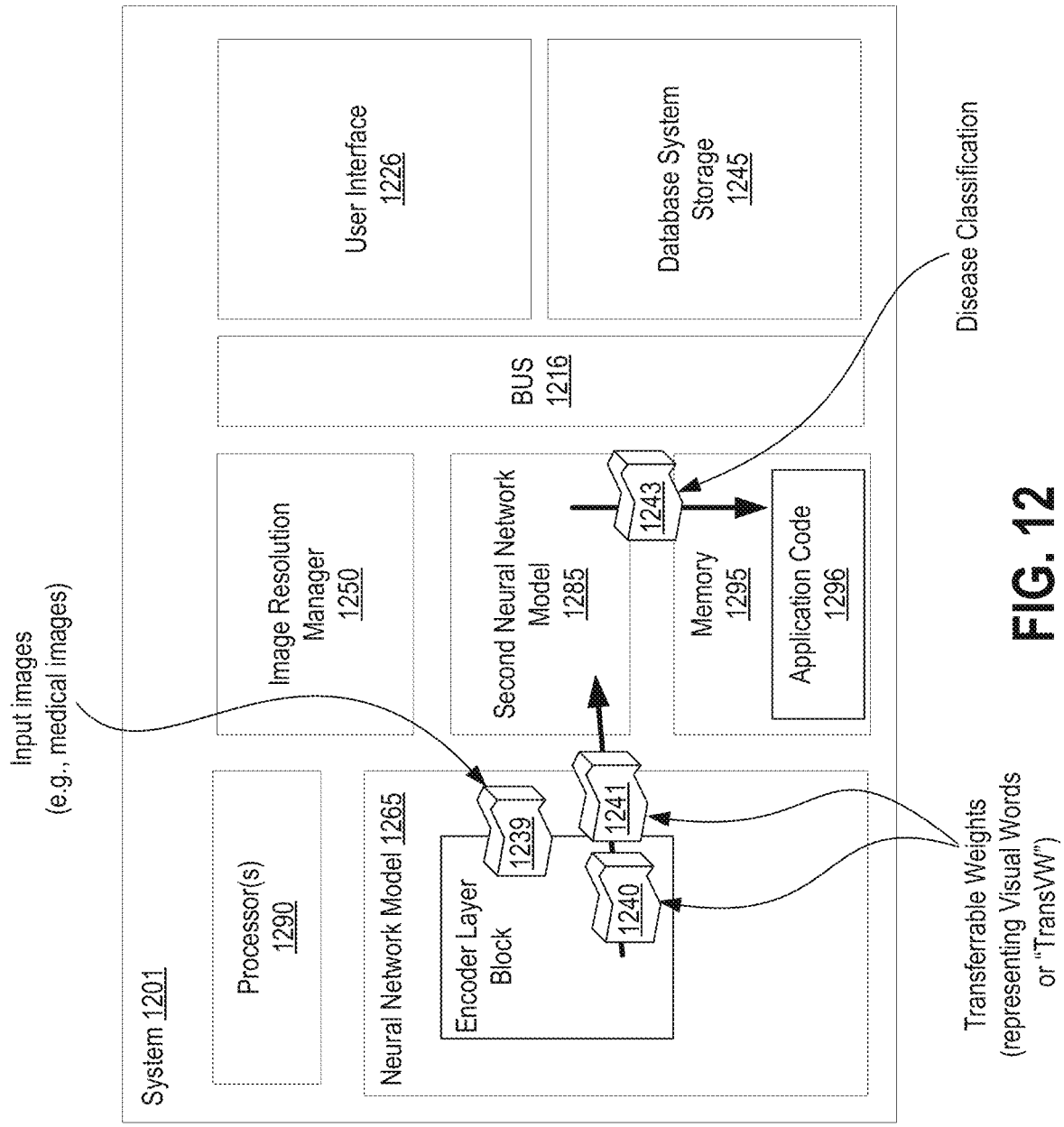
FIG. 12 shows a diagrammatic representation of a system 1201 within which embodiments may operate, be installed, integrated, or configured, in accordance with one embodiment.

FIG. 12 shows a diagrammatic representation of a system 1201 within which embodiments may operate, be installed, integrated, or configured. In accordance with one embodiment, there is a system 1201 having at least a processor 1290 and a memory 1295 therein to execute implementing application code 1296. Such a system 1201 may communicatively interface with and cooperatively execute with the benefit of remote systems, such as a user device sending instructions and data, a user device to receive segmented image 1243 output from the model output manager 1285 of the system, or systems within a networked or within a client-server environment, etc.

According to the depicted embodiment, the system 1201, includes the processor 1290 and the memory 1295 to execute instructions at the system 1201 and wherein the system is specially configured to and operates to execute, via the processor, a Convolutional Neural Network (CNN) model stored within the memory of the system, wherein the CNN model is self-supervised for generalizable and transferable image representation of medical images; identify visual words via the executing CNN model, wherein the visual words are consistent and recurring patterns involving anatomical structures across medical images; transfer learned weights from the CNN model representing identified visual words from an initial CNN model to another CNN model capable of performing the "target task" for diagnosis of disease by fine-tuning the transferred weights, wherein instances of the visual words correspond to sample patches of images extracted across multiple different images for the same visual word, and further wherein the extraction of the instances is performed in via two sub-operations, including: (i) a first sub-operation to execute via the processor of the system by extracting patches around a unique coordinate across all of the available medical images, and (ii) a second sub-operation to execute via the processor of the system by generating patches from an entire image to localize visual words; select the top-most confident instances and further reducing inconsistencies among extracted instances of a visual word from the first sub-operation; and classify disease in previously unseen medical images using the weights of a third CNN, the Anatomy-aware Dual-task Self-supervised (ADS) Learning model, which are transferred to a target task, after the second CNN model performs the "target task" by fine-tuning the learned weights from the first CNN model.

According to such an embodiment, the system 1201 further includes the processor 1290 to execute a neural network model 1265 stored within the memory 1295 of the system 1201, in which the neural network model 1265 is formed from a plurality of layer blocks and is capable of processing input medical images 1239 and further to transfer learned CNN model weight representing the visual words to a different machine learning model of the system 1201. Specifically, weights from the trained CNN model (e.g., representing what are called Transferable Visual Words (TransVW)" 1240 and 1241 are transferred to the second trained CNN model 1285 capable of performing the "target task" for diagnosis of disease, which results in the ultimate disease classification 1243 being output from the system 12001.

The model output manager 1285 may further transmit output back to a user device or other requestor, for example, via the user interface 1226, including sending a disease classification 1243 output to a user device or other requestor, or such information may alternatively be stored within the database system storage 1245 of the system 1201.

According to another embodiment of the system 1201, a user interface 1226 communicably interfaces with a user client device remote from the system and communicatively interfaces with the system via a public Internet.

Bus 1216 interfaces the various components of the system 1201 amongst each other, with any other peripheral(s) of the system 1201, and with external components such as external network elements, other machines, client devices, cloud computing services, etc. Communications may further include communicating with external devices via a network interface over a LAN, WAN, or the public Internet.

FIG. 13 illustrates a diagrammatic representation of a machine 1301 in the exemplary form of a computer system, in accordance with one embodiment, within which a set of instructions, for causing the machine/computer system 1301 to perform any one or more of the methodologies discussed herein, may be executed. In alternative embodiments, the machine may be connected (e.g., networked) to other machines in a Local Area Network (LAN), an intranet, an extranet, or the public Internet. The machine may operate in the capacity of a server or a client machine in a client-server network environment, as a peer machine in a peer-to-peer (or distributed) network environment, as a server or series of servers within an on-demand service environment. Certain embodiments of the machine may be in the form of a personal computer (PC), a tablet PC, a set-top box (STB), a Personal Digital Assistant (PDA), a cellular telephone, a web appliance, a server, a network router, switch or bridge, computing system, or any machine capable of executing a set of instructions (sequential or otherwise) that specify and mandate the specifically configured actions to be taken by that machine pursuant to stored instructions. Further, while only a single machine is illustrated, the term "machine" shall also be taken to include any collection of machines (e.g., computers) that individually or jointly execute a set (or multiple sets) of instructions to perform any one or more of the methodologies discussed herein.

The exemplary computer system 1301 includes a processor 1302, a main memory 1304 (e.g., read-only memory (ROM), flash memory, dynamic random access memory (DRAM) such as synchronous DRAM (SDRAM) or Rambus DRAM (RDRAM), etc., static memory such as flash memory, static random access memory (SRAM), volatile but high-data rate RAM, etc.), and a secondary memory 1318 (e.g., a persistent storage device including hard disk drives and a persistent database and/or a multi-tenant database implementation), which communicate with each other via a bus 1330. Main memory 1304 includes a first neural network model 1324 for performing the "proxy task" and a second trained CNN model 1323 capable of performing the "target task" for diagnosis of disease based on the transferred weights and a collection of transferable visual words which are represented by the "transferable weights" 1325 as shown here, which collectively are utilized to implement a self-supervised chest x-ray image analysis machine-learning model utilizing transferable visual words in support of the methodologies and techniques described herein. Main memory 1304 and its sub-elements are further operable in conjunction with processing logic 1326 and processor 1302 to perform the methodologies discussed herein.

Processor 1302 represents one or more specialized and specifically configured processing devices such as a microprocessor, central processing unit, or the like. More particularly, the processor 1302 may be a complex instruction set computing (CISC) microprocessor, reduced instruction set computing (RISC) microprocessor, very long instruction word (VLIW) microprocessor, processor implementing other instruction sets, or processors implementing a combination of instruction sets. Processor 1302 may also be one or more special-purpose processing devices such as an application specific integrated circuit (ASIC), a field programmable gate array (FPGA), a digital signal processor (DSP), network processor, or the like. Processor 1302 is configured to execute the processing logic 1326 for performing the operations and functionality which is discussed herein.

The computer system 1301 may further include a network interface card 1308. The computer system 1301 also may include a user interface 1310 (such as a video display unit, a liquid crystal display, etc.), an alphanumeric input device 1312 (e.g., a keyboard), a cursor control device 1313 (e.g., a mouse), and a signal generation device 1316 (e.g., an integrated speaker). The computer system 1301 may further include peripheral device 1336 (e.g., wireless or wired communication devices, memory devices, storage devices, audio processing devices, video processing devices, etc.).

The secondary memory 1318 may include a non-transitory machine-readable storage medium or a non-transitory computer readable storage medium or a non-transitory machine-accessible storage medium 1331 on which is stored one or more sets of instructions (e.g., software 1322) embodying any one or more of the methodologies or functions described herein. The software 1322 may also reside, completely or at least partially, within the main memory 1304 and/or within the processor 1302 during execution thereof by the computer system 1301, the main memory 1304 and the processor 1302 also constituting machine-readable storage media. The software 1322 may further be transmitted or received over a network 1320 via the network interface card 1308.

While the subject matter disclosed herein has been described by way of example and in terms of the specific embodiments, it is to be understood that the claimed embodiments are not limited to the explicitly enumerated embodiments disclosed. To the contrary, the disclosure is intended to cover various modifications and similar arrangements as are apparent to those skilled in the art. Therefore, the scope of the appended claims is to be accorded the broadest interpretation so as to encompass all such modifications and similar arrangements. It is to be understood that the above description is intended to be illustrative, and not restrictive. Many other embodiments will be apparent to those of skill in the art upon reading and understanding the above description. The scope of the disclosed subject matter is therefore to be determined in reference to the appended claims, along with the full scope of equivalents to which such claims are entitled.

What is claimed is:

1. A method performed by a system having at least a processor and a memory therein to execute instructions, wherein the method comprises:
    executing, via the processor, a Convolutional Neural Network (CNN) model stored within the memory of the system, wherein the CNN model is self-supervised for generalizable and transferable image representation of medical images;
    identifying visual words via the executing CNN model, wherein the visual words are consistent and recurring patterns involving anatomical structures across medical images;
    transferring learned weights from the CNN model representing identified visual words from an initial CNN model to another CNN model capable of performing the "target task" for diagnosis of disease by fine-tuning the transferred weights, wherein instances of the visual words correspond to sample patches of images extracted across multiple different images for the same visual word, and further wherein the extraction of the instances is performed in via two sub-operations, including: (i) a first sub-operation to execute via the processor of the system by extracting patches around a unique coordinate across all of the available medical images, and (ii) a second sub-operation to execute via the processor of the system by generating patches from an entire image to localize visual words;
    selecting the top-most confident instances and further reducing inconsistencies among extracted instances of a visual word from the first sub-operation; and
    classifying disease in previously unseen medical images using the weights of a third CNN, the Anatomy-aware Dual-task Self-supervised (ADS) Learning model, which are transferred to a target task, after the second CNN model performs the "target task" by fine-tuning the learned weights from the first CNN model.

2. The method of claim 1, wherein a target CNN model is fine-tuned to be capable of performing identification of X-ray image elements and diagnosis of diseases within such X-ray images for never before seen X-ray images which are not part of any training dataset.

3. The method of claim 1, further comprising:
    classifying disease in previously unseen medical images by performing identification of X-ray image elements and diagnosis of diseases within such X-ray images for never before seen X-ray images which are not part of any training dataset.

4. The method of claim 1, wherein the medical images are not manually annotated.

5. The method of claim 1, wherein the medical images are chest X-ray medical images.

6. The method of claim 1, wherein the learned model is transferred to a target application that classifies thorax disease, wherein the disease is present in chest X-rays.

7. The method of claim 1, wherein a first sub-operation implements coordinate-based visual word (CVW) learning, including:
 selecting, at random, a medical image to serve as a reference image for a visual word, wherein the visual word is assigned a visual word ID i;
 identifying, via an image registration technique, the top N-most similar images to the selected reference image from an image dataset, wherein N is the number of instances of each visual word;
 extracting patches at a randomly-generated unique coordinate across the top N-most similar images;
 repeating extraction for all visual words of interest; and
 training the CVW classifier to classify the visual words into M classes, wherein M is the number of visual word classes.

8. The method of claim 7, wherein the unique coordinate is randomly generated at an $i^{th}$ coordinate.

9. The method of claim 1, wherein the second sub-operation further comprises applying an Anatomy-aware visual word (AVW) learning model, including:
 generating image patches, wherein the image patches are generated by sliding a window on each image in a given training set;
 inputting the generated patches to the CVW classifier to localize visual words in each image;
 selecting the top K-most confident instances of each visual word among all images, wherein K is the number for instances of each visual word; and
 training an AVW classifier to classify the visual words into M classes, wherein M is the number of visual word classes.

10. The method of claim 9:
 wherein the AVW classifier serves as an encoder for a self-supervised U-Net-like dual-task learner network, the network comprising a deformed visual word input, wherein the deformed visual word is generated by applying elastic transformation on a visual word, wherein elastic transformation involves spatial-level deformation of the visual word input; and
 wherein an Anatomy-aware Dual-task Self-supervised (ADS) learning process deforms each input visual word instance using elastic transformation.

11. Non-transitory computer readable storage media having instructions stored thereupon that, when executed by a system having at least a processor and a memory therein, the instructions cause the system to perform operations including:
 executing, via the processor, a Convolutional Neural Network (CNN) model stored within the memory of the system, wherein the CNN model is self-supervised for generalizable and transferable image representation of medical images;
 identifying visual words via the executing CNN model, wherein the visual words are consistent and recurring patterns involving anatomical structures across medical images;
 transferring learned weights from the CNN model representing identified visual words from an initial CNN model to another CNN model capable of performing the "target task" for diagnosis of disease by fine-tuning the transferred weights, wherein instances of the visual words correspond to sample patches of images extracted across multiple different images for the same visual word, and further wherein the extraction of the instances is performed in via two sub-operations, including: (i) a first sub-operation to execute via the processor of the system by extracting patches around a unique coordinate across all of the available medical images, and (ii) a second sub-operation to execute via the processor of the system by generating patches from an entire image to localize visual words;
 selecting the top-most confident instances and further reducing inconsistencies among extracted instances of a visual word from the first sub-operation; and
 classifying disease in previously unseen medical images using the weights of a third CNN, the Anatomy-aware Dual-task Self-supervised (ADS) Learning model, which are transferred to a target task, after the second CNN model performs the "target task" by fine-tuning the learned weights from the first CNN model.

12. The non-transitory computer readable storage media of claim 11, wherein a target CNN model is fine-tuned to be capable of performing identification of X-ray image elements and diagnosis of diseases within such X-ray images for never before seen X-ray images which are not part of any training dataset.

13. The non-transitory computer readable storage media of claim 11, wherein the medical images are not manually annotated.

14. The non-transitory computer readable storage media of claim 11, wherein the neural network model has not been pre-trained (with ImageNet).

15. The non-transitory computer readable storage media of claim 11, wherein the medical images are chest X-ray medical images.

16. The non-transitory computer readable storage media of claim 11, wherein the learned model classifies thorax disease (in chest X-rays).

17. The non-transitory computer readable storage media of claim 11, wherein the first sub-operation further comprises coordinate-based visual word (CVW) learning, including:
 selecting, at random, a medical image to serve as a reference image for the visual word, wherein the visual word is assigned a visual word ID i;
 identifying, via an algorithm, the top N-most similar images to the selected reference image from an image dataset, wherein N is the number of instances of each visual word;
 extracting patches at a randomly-generated unique coordinate across the top N-most similar images;
 repeating extraction for all visual words of interest; and
 training a CVW classifier to classify the visual words into M classes, wherein M is the number of visual word classes.

18. The non-transitory computer readable storage media of claim 11, wherein the second sub-operation further comprises applying an Anatomy-aware visual word (AVW) learning model, including:
 generating image patches, wherein the image patches are generated by sliding a window on each image in a given training set;

inputting the generated patches to a CVW classifier to localize visual words in each patch;

selecting the top K-most confident instances among all images, wherein K is the number for instances of each visual word;

training an AVW classifier to classify the visual words into M classes, wherein M is the number of visual word classes;

wherein the AVW classifier serves as an encoder for a self-supervised U-Net-like dual-task learner network, the network comprising (i) a deformed visual word input, wherein the deformed visual word is generated by applying elastic transformation on a visual word, wherein elastic transformation involves spatial-level deformation of the visual word input and (ii) the AVW classifier receiving the input and acting as a pre-trained encoder to perform dual-task visual word classification and restoration simultaneously; and a dual-task output comprising a visual word ID and reconstructed visual word instance;

wherein improving representational learning of image context through Anatomy-aware Dual-task Self-supervised (ADS) learning.

19. A system comprising:

a memory to store instructions;

a processor to execute the instructions stored in the memory;

wherein the system is specially configured to:

execute, via the processor, a Convolutional Neural Network (CNN) model stored within the memory of the system, wherein the CNN model is self-supervised for generalizable and transferable image representation of medical images;

identify visual words via the executing CNN model, wherein the visual words are consistent and recurring patterns involving anatomical structures across medical images;

transfer learned weights from the CNN model representing identified visual words from an initial CNN model to another CNN model capable of performing the "target task" for diagnosis of disease by fine-tuning the transferred weights, wherein instances of the visual words correspond to sample patches of images extracted across multiple different images for the same visual word, and further wherein the extraction of the instances is performed in via two sub-operations, including: (i) a first sub-operation to execute via the processor of the system by extracting patches around a unique coordinate across all of the available medical images, and (ii) a second sub-operation to execute via the processor of the system by generating patches from an entire image to localize visual words;

select the top-most confident instances and further reducing inconsistencies among extracted instances of a visual word from the first sub-operation; and classify disease in previously unseen medical images using the weights of a third CNN, the Anatomy-aware Dual-task Self-supervised (ADS) Learning model, which are transferred to a target task, after the second CNN model performs the "target task" by fine-tuning the learned weights from the first CNN model.

20. The system of claim 19, wherein a target CNN model is fine-tuned to be capable of performing identification of X-ray image elements and diagnosis of diseases within such X-ray images for never before seen X-ray images which are not part of any training dataset.

* * * * *